US006300501B1

(12) United States Patent
Dobrusin et al.

(10) Patent No.: US 6,300,501 B1
(45) Date of Patent: *Oct. 9, 2001

(54) HISTIDINE-(N-BENZYL GLYCINAMIDE) INHIBITORS OF PROTEIN FARNESYL TRANSFERASE

(75) Inventors: Ellen M. Dobrusin; Annette M. Doherty; James S. Kaltenbronn; Daniele M. Leonard; Dennis J. McNamara; Judith Sebolt-Leopold, all of Ann Arbor; Kevon R. Shuler, Chelsea, all of MI (US)

(73) Assignee: Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,241

(22) PCT Filed: Apr. 29, 1997

(86) PCT No.: PCT/US97/06591

§ 371 Date: Nov. 2, 1998

§ 102(e) Date: Nov. 2, 1998

(87) PCT Pub. No.: WO97/44350

PCT Pub. Date: Nov. 27, 1997

Related U.S. Application Data

(60) Provisional application No. 60/016,110, filed on May 22, 1996.

(51) Int. Cl.$^7$ ............ C07D 217/06; C07D 233/54; C07D 233/64; C07K 5/06; A61K 31/417; A61K 31/44; A61K 38/05

(52) U.S. Cl. .............. 546/146; 514/18; 514/19; 514/94; 514/311; 514/399; 548/338.1; 548/343.1

(58) Field of Search .............. 548/343.1, 338.1; 514/18, 19, 94, 311, 399; 546/146

(56) References Cited

U.S. PATENT DOCUMENTS

| 4,826,815 | * | 5/1989 | Luly et al. ............... 514/19 |
| 4,857,650 | * | 8/1989 | Iizuka et al. ........... 548/338.1 |
| 4,985,407 | * | 1/1991 | Foxton et al. ............ 514/19 |
| 5,036,048 | * | 7/1991 | Watkins ................... 514/16 |
| 5,304,604 | * | 4/1994 | Davidson et al. ........ 514/238.2 |
| 5,571,792 | * | 11/1996 | Bolton et al. ............ 514/18 |

FOREIGN PATENT DOCUMENTS

| 94/00419 | 1/1994 | (WO) . |
| 95/09001 | 4/1995 | (WO) . |
| 95/12612 | 5/1995 | (WO) . |
| 96/00736 | 1/1996 | (WO) . |
| 97/44350 | 11/1997 | (WO) . |

OTHER PUBLICATIONS

McNamara, D. J., et al., "Histidyl–(N–Benzylglycinamides) as Ras Farnesyltransferase Inhibitors Possessing Antitumor Activity in Mice," 213$^{th}$ *American Chemical Society National Meeting*, San Francisco, CA, Apr. 13–17, 1997.

Kaltenbronn, J. S., et al., "Histidine–(N–Benzylglycinamides): Structure–Activity Studies Optimizing Potency Against Ras Farnesyl Transferase," *American Association of Cancer Research*, Apr. 15, 1997, poster presentation.

* cited by examiner

*Primary Examiner*—Floyd D. Higel
(74) *Attorney, Agent, or Firm*—Charles W. Ashbrook

(57) ABSTRACT

Inhibitors of protein farnesyl transferase enzymes are described, as well as methods for the preparation and pharmaceutical compositions of the same, which are useful in treating cancer, restenosis, psoriasis, endometriosis, atherosclerosis, or viral infections.

29 Claims, No Drawings

HISTIDINE-(N-BENZYL GLYCINAMIDE) INHIBITORS OF PROTEIN FARNESYL TRANSFERASE

This application is a 371 of PCT/US97/06591 filed Apr. 27, 1997. This application claims the benefit of U.S. Provisional Application No. 60/016,110 filed May 22, 1996.

The present invention relates to compounds that can be used in the medicinal field to treat, prophylactically or otherwise, uncontrolled or abnormal proliferation of human tissues. Specifically, the present invention relates to compounds that inhibit the farnesyl transferase enzyme, which has been determined to activate ras proteins that in turn activate cellular division and are implicated in cancer and restenosis.

BACKGROUND OF THE INVENTION

Ras protein (or p21) has been examined extensively because mutant forms are found in 20% of most types of human cancer and greater than 50t of colon and pancreatic carcinomas (Gibbs J. B., *Cell*, 1991;65:1, Cartwright T., et al., *Chimica Oggi*, 1992;10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J., et al., *Microbiol. Rev.*, 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis is such a condition. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J., et al., *Hypertension*, 1989;13:706 and *J. Clin. Invest.*, 83:1419; Gibbons G. H., et al., *Hypertension*, 1989;14:358; Satoh T., et al., *Molec. Cell. Biol.*, 1993;13:3706). The fact that ras proteins are known to be involved in cell division processes makes them a candidate for intervention in many situations where cells are dividing uncontrollably. In direct analogy to the inhibition of mutant ras related cancer, blockade of ras dependant processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyl transferase (PFT). This consensus sequence consists of a cysteine residue located four amino acids from the carboxyl terminus, followed by two lipophilic amino acids, and the C-terminal residue. The sulfhydryl group of the cysteine residue is alkylated by farnesylpyrophosphate in a reaction that is catalyzed by protein farnesyl transferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F., et al., *Cell*, 1989;57:1617, Schafer W. R., et al., *Science*, 1989;245:379, Casey P. J., *Proc. Natl. Acad. Sci. USA*, 1989;86:8323).

Recently, protein farnesyl transferases (PFTs, also referred to as farnesyl proteintransferases (FPTs) have been identified and a specific PFT from rat brain was purified to homogeneity (Reiss Y., et al., *Bioch. Soc. Trans.*, 1992;20:487–88). The enzyme was characterized as a heterodimer composed of one alpha-subunit (49 kDa) and one beta-subunit 146 kDa), both of which are required for catalytic activity. High level expression of mammalian PFT in a baculovirus system and purification of the recombinant enzyme in active form has also been accomplished (Chen W.-J., et al., *J. Biol. Chem.*, 1993;268:9675).

In light of the foregoing, the discovery that the function of oncogenic ras proteins is critically dependent on their post-translational processing provides a means of cancer chemotherapy through inhibition of the processing enzymes. The identification and isolation of a protein farnesyl transferase that catalyzes the addition of a farnesyl group to ras proteins provides a promising target for such intervention. Ras farnesyl transferase inhibitors have been shown to have anticancer activity in several recent articles.

Ras inhibitor agents act by inhibiting farnesyl transferase, the enzyme that anchors the protein product of the ras gene to the cell membrane. The role of the ras mutation in transducing growth signals within cancer cells relies on the protein being in the cell membrane so with farnesyl transferase inhibited, the ras protein will stay in the cytosol and be unable to transmit growth signals: these facts are well-known in the literature.

A peptidomimetic inhibitor of farnesyl transferase B956 and its methyl ester B1086 at 100 mg/kg have been shown to inhibit tumor growth by EJ-1 human bladder carcinoma, HT1080 human fibrosarcoma and human colon carcinoma xenografts in nude mice (Nagasu, T., et al., *Cancer Res.*, 1995;55:5310–5314). Furthermore, inhibition of tumor growth by B956 has been shown to correlate with inhibition of ras posttranslational processing in the tumor. Other ras farnesyl transferase inhibitors have been shown to specifically prevent ras processing and membrane localization and are effective in reversing the transformed phenotype of mutant ras containing cells (Sepp-Lorenzino L., et al., *Cancer Res.*, 1995;55:5302–5309).

In another report (Sun J., et al., *Cancer Res.*, 1995;55:4243–4247), a ras farnesyl transferase inhibitor FTI276 has been shown to selectively block tumor growth in nude mice of a human lung carcinoma with K-ras mutation and p53 deletion. In yet another report, daily administration of a ras farnesyl transferase inhibitor L-744,832 caused tumor regression of mammary and salivary carcinomas in ras transgenic mice (Kohl et al., *Nature Med.*, 1995;1(8)

:792–748). Thus, ras farnesyl transferase inhibitors have benefit in certain forms of cancer, particularly those dependent on oncogenic ras for their growth. However, it is well-known that human cancer is often manifested when several mutations in important genes occurs, one or more of which may be responsible for controlling growth and metastases. A single mutation may not be enough to sustain growth and only after two of three mutations occur, tumors can develop and grow. It is therefore difficult to determine which of these mutations may be primarily driving the growth in a particular type of cancer. Thus, ras farnesyl transferase inhibitors can have therapeutic utility in tumors not solely dependent on oncogenic forms of ras for their growth. For example, it has been shown that various ras FT-inhibitors have antiproliferative effects in vivo against tumor lines with either wild-type or mutant ras (Sepp-Lorenzino, supra.). In addition, there are several ras-related proteins that are prenylated. Proteins such as R-Ras2/TC21 are ras-related proteins that are prenylated in vivo by both farnesyl transferase and geranylgeranyl transferase I (Carboni, et al., *Oncogene*, 1995;10:1905–1913). Therefore, ras farnesyl transferase inhibitors could also block the prenylation of the above proteins and therefore would then be useful in inhibiting the growth of tumors driven by other oncogenes.

With regard to the restenosis and vascular proliferative diseases, it has been shown that inhibition of cellular ras prevents smooth muscle proliferation after vascular injury in vivo (Indolfi C, et al., *Nature Med.*, 1995;1(6):541–545). This report definitively supports a role for farnesyl transferase inhibitors in this disease, showing inhibition of accumulation and proliferation of vascular smooth muscle.

SUMMARY OF THE INVENTION

The present invention provides compounds having the Formula I

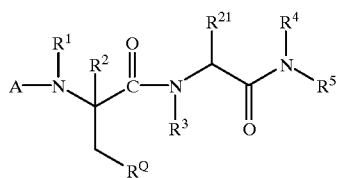

I wherein
$R^{21}$ is hydrogen or $C_1$–$C_6$ alkyl;
RQ is

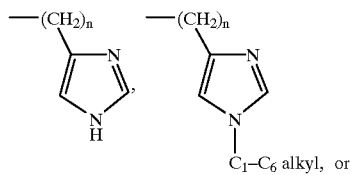 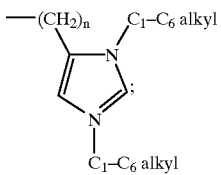

n is 0 or 1;

A is —$COR^a$, —$CO_2R^{a'}$, —$CONHR^{a'}$, —$CSR^a$, —$C(S)OR^{a'}$, —$C(S)NHR^{a'}$, $SO_2R^a$, —$CONR^aR^{a''}$,

or

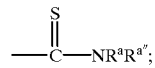

$R^a$, $R^{a'}$, and $R^{a''}$ are independently $C_1$–$C_6$ alkyl, —$(CH_2)_m$-cycloalkyl, —$(CH_2)_m$-aryl, or —$(CH_2)_m$-heteroaryl;
each m is independently 0 to 3;
$R^1$, $R^2$, and $R^4$ are independently hydrogen or $C_1$–$C_6$ alkyl;

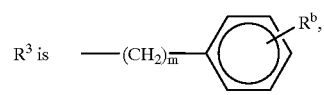

—$(CH_2)_m$-heteroaryl,

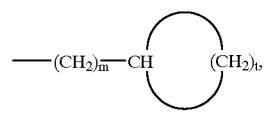

—$(CH_2)_m$-naphthyl, —$(CH_2)_m$(heteroaryl substituted with $R^b$), or $C_1$–$C_6$ alkyl;
t is 2 to 6;
$R^b$ is —O-phenyl, —O-benzyl, halogen, $C_1$–$C_6$ alkyl, hydrogen, —O—$C_1$–$C_6$ alkyl, —$NH_2$, —$NHR^a$, $NR^aR^{a'}$, $\overset{O}{\underset{\|}{-C}}C_1$–$C_6$ alkyl, $\overset{O}{\underset{\|}{-C}}$—aryl, —OH, —$CF_3$, —$NO_2$, $\overset{O}{\underset{\|}{-C}}OH$, $\overset{O}{\underset{\|}{-C}}OC_1$–$C_6$ alkyl, —CN, —$OPO_3H_2$, —$CH_2PO_3H_2$, $\overset{O}{\underset{\|}{-C}}O$aryl, —$N_3$, —$CF_2CF_3$, —$SO_2R^a$, —$SO_2NR^aR^{a'}$, —CHO, —$OCOCH_3$, or —$O(CH_2)_m$-heteroaryl, $\overset{O}{\underset{\|}{-C}}NR^aR^{a'}$, —NH—$\overset{O}{\underset{\|}{C}}$—$R^a$, —O—$(CH_2)_yNR^aR^{a'}$;
—$O(CH_2)_m$-cycloalkyl, —$(CH_2)_m$-cycloalkyl, —O—$(CH_2)_m$-aryl, —$(CH_2)_m$-aryl, or —$(CH_2)_m$-heteroaryl;
y is 2 or 3;

$R^5$ is

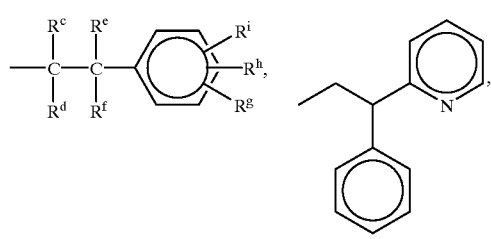,

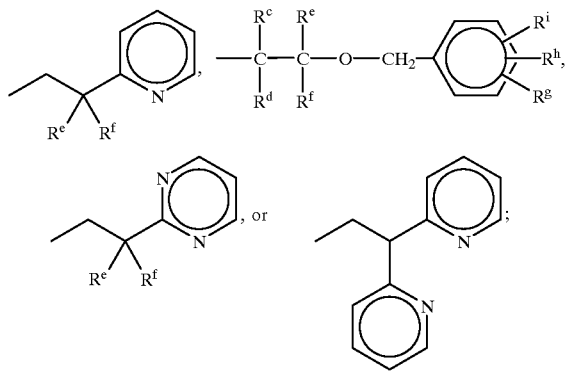, or

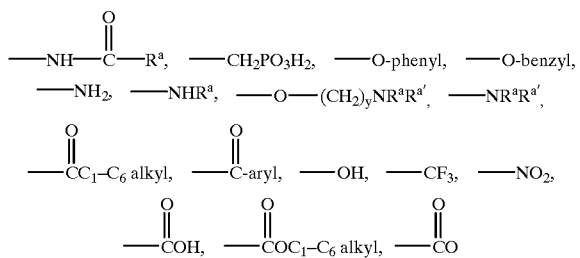;

$R^i$, $R^g$, and $R^h$ are independently hydrogen, halogen, —$OC_1$–$C_6$ alkyl, $C_1$–$C_6$ alkyl, —CN, —$OPO_3H_2$, —NH—C(=O)—$R^a$, —$CH_2PO_3H_2$, —O-phenyl, —O-benzyl, —$NH_2$, —$NHR^a$, —O—$(CH_2)_y NR^a R^{a'}$, —$NR^a R^{a'}$, —C(=O)$C_1$–$C_6$alkyl, —C(=O)-aryl, —OH, —$CF_3$, —$NO_2$, —COH, —CO$C_1$–$C_6$alkyl, —CO(=O), —$N_3$, —$CF_2CF_3$, $SO_2R^a$, —$SO_2NR^a R^{a'}$, —CHO, or —$OCOCH_3$; and $R^c$, $R^d$, $R^e$, and $R^f$ are independently $C_1$–$C_6$ alkyl, —$(CH_2)_m$-phenyl, hydrogen, —$(CH_2)_m$—OH, —$(CH_2)_m NH_2$, —$(CH_2)_m$-cycloalkyl, or —CN, and the pharmaceutically acceptable salts, esters, amides, and prodrugs thereof.

In a preferred embodiment of the compounds of Formula I $R^1$ is hydrogen, $R^2$ is hydrogen, $R^4$ is hydrogen, $R^{21}$ is hydrogen or $CH_3$; and A is

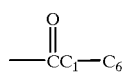

-continued

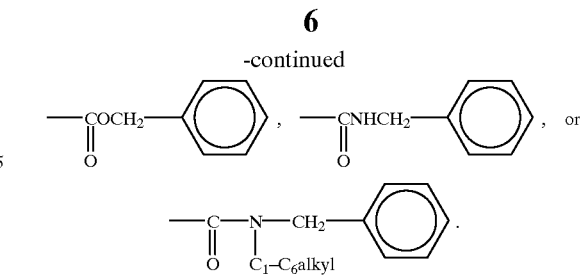

In another preferred embodiment of the compound of Formula I

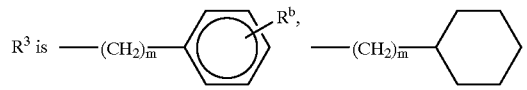

or —$CH_2$—$CH(CH_3)_2$.

$R^1$ is hydrogen, $R^2$ is hydrogen, $R^4$ is hydrogen, and $R^{21}$ is hydrogen or $CH_3$.

In another preferred embodiment of the compounds of Formula I $R^5$ is

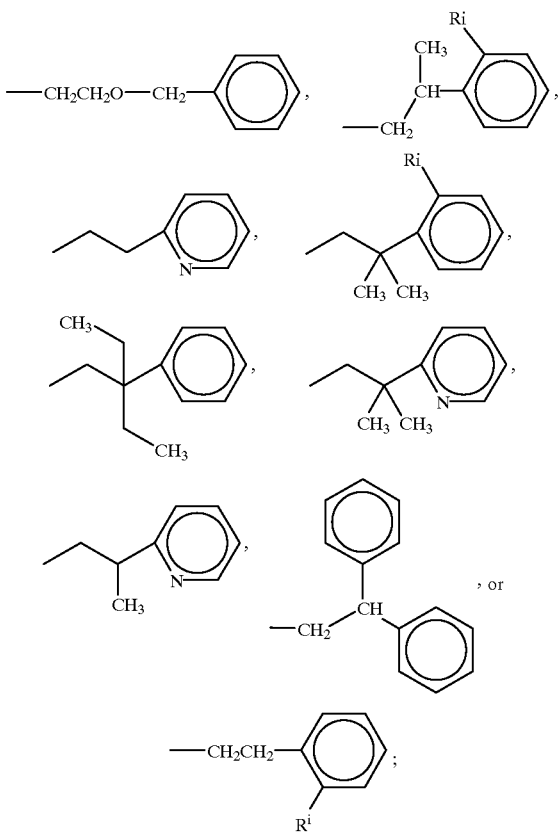

where $R^i$ is hydrogen, Cl, Br, F, or $NH_2$.

Also provided are compounds having the Formula II

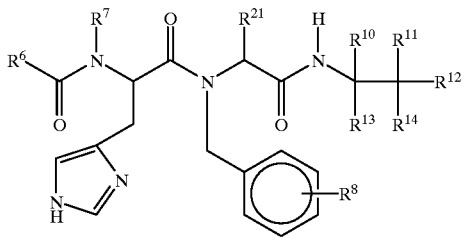

wherein
R$^6$ is —O-benzyl, —NH-benzyl, or

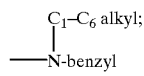

R$^{21}$ is hydrogen or methyl;
R$^7$ is hydrogen or methyl;
R$^8$ is hydrogen, halogen, C$_1$–C$_6$ alkyl, —O-benzyl, —OC$_1$–C$_6$ alkyl, —CF$_3$, —OH, —O—(CH$_2$)$_m$-pyridyl, or phenyl;
R$^{10}$, R$^{11}$, R$^{13}$, and R$^{14}$ are independently hydrogen, C$_1$–C$_6$ alkyl, or —(CH$_2$)$_m$-phenyl;
each m is independently 0 to 3;
R$^{12}$ is

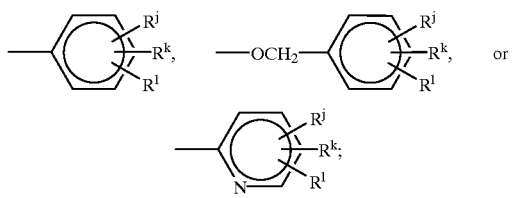

and
R$^j$, R$^k$, and R$^l$ are independently hydrogen, halogen, —OC$_1$–C$_6$ alkyl, —C$_1$–C$_6$ alkyl, —NHR$^a$, or NH$_2$, and the pharmaceutically acceptable salts, esters, amides, and prodrugs thereof.

In a preferred embodiment of the compounds of Formula II, R$^{11}$ and R$^{14}$ are methyl.

In another preferred embodiment of the compounds of Formula II, R$^8$ is methyl or methoxy.

Also provided are compounds having the Formula III

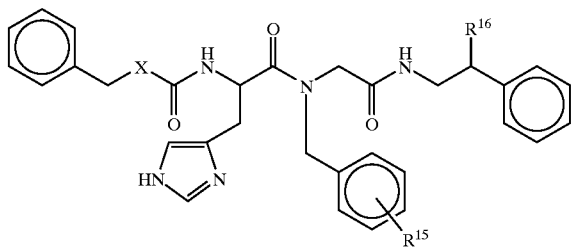

wherein
X is NH, O, or —N(CH$_3$);

R$^{15}$ is —O-benzyl, —CF$_3$, hydrogen, halogen, —OC$_1$–C$_6$ alkyl, phenyl, —O—(CH$_2$)$_m$-pyridyl, or —C$_1$–C$_6$ alkyl;
m is 0 to 3; and
R$^{16}$ is a phenyl, hydrogen, or C$_1$–C$_6$ alkyl, and the pharmaceutically acceptable salts, esters, amides, and prodrugs thereof.

Also provided are compounds having the Formula IV:

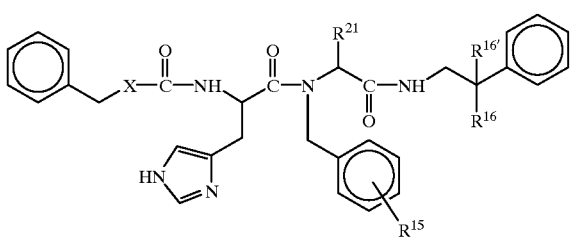

wherein
X is NH, O, or N(CH$_3$);
R$^{15}$ is —O-benzyl, —CF$_3$, hydrogen, halogen, C$_1$–C$_6$ alkyl, —O—C$_1$–C$_6$ alkyl, phenyl, or —O—(CH$_2$)$_m$-pyridyl;
R$^{16}$ and R$^{16'}$ are C$_1$–C$_6$ alkyl;
m is 0 to 3; and
R$^{21}$ is hydrogen or methyl, and the pharmaceutically acceptable salts, esters, amides, and prodrugs thereof.

In another aspect, the present invention provides a pharmaceutically acceptable composition that comprises a compound of Formula I, II, III, or IV.

Also provided is a method of treating or preventing restenosis, the method comprising administering to a patient having restenosis or a risk of having restenosis a therapeutically effective amount of a compound of Formula I, II, III, or IV.

Also provided is a method of treating cancer, the method comprising administering to a patient having cancer a therapeutically effective amount of a compound of Formula I, II, III, or IV.

Also provided is a method of treating psoriasis, the method comprising administering to a patient having psoriasis a therapeutically effective amount of a compound of Formula I, II, III, or IV.

Also provided is a method of treating viral infection, the method of comprising administering to a patient having a viral infection a therapeutically effective amount of a compound of Formula I, II, III, or IV.

In a more preferred embodiment, the cancer is lung cancer, colon cancer, breast cancer, pancreatic cancer, thyroid cancer, or bladder cancer.

In a most preferred embodiment, the compounds of Formula I, II, III, or IV are
  (S)-[1-[(4-Benzyloxy-benzyl)-(phenethyl-carbamoyl-methyl)-carbamoyl]-2-(3H-imidazole-4-yl)-ethyl)-carbamic acid benzyl ester;
  (S)-[1-[[2-Benzyloxy-ethylcarbamoyl]-methyl]-[4-chlorobenzyl]-carbamoyl]-2-(1H-imidazole-4-yl)-ethyl]-carbamic acid benzyl ester;
  (S)-1-[(4-Benzyloxy-benzyl)-[(2-phenyl-propylcarbamoyl)-methyl)-carbamoyl]-2-(1H-imidazole-4-yl)-ethyl]carbamic acid benzyl ester;
  (S)-[1-[(4-Benzyloxy-benzyl)-[(2,2-diphenylethylcarbamoyl)-methyl]-carbamoyl]-2-(1H-imidazole-4-yl)-ethyl]-carbamic acid benzyl ester;

(S)-N-(4-Benzyloxy-benzyl)-2-(3-benzyl-ureido)-3-(1H-imidazole-4-yl)-N-[(2-phenyl-propylcarbamoyl)-methyl]-propionamide;

(S)-[1-{Biphenyl-4-ylmethyl-[(2-methyl-2-phenylpropylcarbamoyl)-methyl]-carbamoyl}-2-(1H-imidazole-4-yl)-ethyl]-carbamic acid benzyl ester;

(S)-[1-{Biphenyl-4-ylmethyl-[(2-phenylpropylcarbamoyl)-methyl]-carbamoyl}-2-(lH-imidazole-4-yl)-ethyl]-carbamic acid benzyl ester;

(S)-[1-((4-Benzyloxy-benzyl)-{[2-(2-fluorophenyl)-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(2-pyridin-2-yl-ethylcarbamoyl)-methyl]-carbamoyl}-2-(1H-imidazole-4-yl)-ethyl]-carbamic acid benzyl ester;

(S)-[1-((4-Benzyloxy-benzyl)-{[2-(2-bromo-phenyl)-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(1-methyl-2-phenyl-ethylcarbamoyl)-methyl]-carbamoyl}-2-(1H-imidazole-4-yl)-ethyl]-carbamic acid benzyl ester;

(S)-[1-{(4-Benzyloxy-benzyl)-[(2-phenyl-2-pyridin-2-yl-ethylcarbamoyl)-methyl]-carbamoyl}-2-(1H-imidazole-4-yl)-ethyl]-carbamic acid benzyl ester;

(S)-[1-{(4-Chloro-benzyl)-[(2-phenyl-propylcarbamoyl)-methyl]-carbamoyl}-2-(1H-imidazole-4-yl)-ethyl]-carbamic acid benzyl ester;

(S)-[1-{(4-Benzyloxy-benzyl)-[(2-phenyl-butylcarbamoyl)-methyl]-carbamoyl}-2-(1H-imidazole-4-yl)-ethyl]-carbamic acid benzyl ester;

(S)-N-(4-Benzyloxy-benzyl)-3-(1H-imidazole-4-yl)-2-(3-phenyl-propionylamino)-N-[(2-phenyl-propylcarbamoyl)-methyl]-propionamide;

(S)-[1-{(4-Fluoro-benzyl)-[(2-phenyl-propyl-carbamoyl)-methyl]-carbamoyl}-2-(1H-imidazole-4-yl)-ethyl]-carbamic acid benzyl ester;

(S)-(2-(1H-Imidazole-4-yl)-1-{(4-methyl-benzyl)-[(2-phenyl-propylcarbamoyl)-methyl]-carbamoyl)-ethyl}-carbamic acid benzyl ester;

(S)-(2-(1H-Imidazole-4-yl)-1-{(4-methoxy-benzyl)-[(2-phenyl-propylcarbamoyl)-methyl]-carbamoyl}-ethyl)-carbamic acid benzyl ester;

(S)-[1-[{[2-(2-Amino-phenyl)-propylcarbamoyl]-methyl}-(4-benzyloxy-benzyl)-carbamoyl]-2-(3H-imidazole-4-yl)-ethyl]-carbamic acid benzyl ester;

(S)-[1-{(4-Fluoro-benzyl)-[(2-methyl-2-phenyl-propylcarbamoyl)-methyl]-carbamoyl}-2-(1H-imidazole-4-yl)-ethyl]-carbamic acid benzyl ester;

(S)-[1-{Benzyl-[(2-phenyl-propylcarbamoyl)-methyl]-carbamoyl}-2-(1H-imidazole-4-yl)-ethyl]-carbamic acid benzyl ester;

(S)-[1-((4-Benzyloxy-benzyl)-{[2-(2-chloro-phenyl)-2-phenyl-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(2-ethyl-2-phenyl-butylcarbamoyl)-methyl]-carbamoyl}-2-(3H-imidazole-4-yl)-ethyl]-carbamic acid benzyl ester;

(S)-N-(4-Benzyloxy-benzyl)-2-(3-benzyl-ureido)-3-(1H-imidazole-4-yl)-N-[(2-phenyl-propylcarbamoyl)-methyl]-propionamide;

(S)-N-(4-Benzyloxy-benzyl)-2-(3-benzyl-ureido)-3-(1H-imidazole-4-yl)-N-[(2-phenyl-butylcarbamoyl)-methyl]-propionamide;

(S)-[1-{(2-Chloro-benzyl)-[(2-phenyl-propylcarbamoyl)-methyl]-carbamoyl)-2-(1H-imidazole-4-yl)-ethyl]-carbamic acid benzyl ester;

(S)-[1-{(4-Bromo-benzyl)-[(2-phenyl-propylcarbamoyl)-methyl]-carbamoyl}-2-(1H-imidazole-4-yl)-ethyl]-carbamic acid benzyl ester;

(S)-[1-{(3-Chloro-benzyl)-[(2-phenyl-propylcarbamoyl)-methyl)]-carbamoyl}-2-(1H-imidazole-4-yl)-ethyl]-carbamic acid benzyl ester;

(S)-[1-{(4-Chloro-benzyl)-[(2-methyl-2-phenyl-propylcarbamoyl)-methyl]-carbamoyl}-2-(1H-imidazole-4-yl)-ethyl)-carbamic acid benzyl ester;

(S)-[1-((4-Benzyloxy-benzyl)-{[2-(2-chloro-phenyl)-propylcarbamoyl]-methyl}-carbamoyl)-2-(1H-imidazole-4-yl)-ethyl]-carbamic acid benzyl ester;

(S)-(2-(1H-Imidazole-4-yl)-1-{(2-methoxy-benzyl)-[(2-phenyl-propylcarbamoyl)-methyl]-carbamoyl)}-ethyl)-carbamic acid benzyl ester;

(S)-(2-(1H-Imidazole-4-yl)-1-{[(2-phenyl-propylcarbamoyl)-methyl)]-[4-(pyridin-4-ylmethoxy)-benzyl]-carbamoyl}-ethyl)-carbamic acid benzyl ester;

(S)-(2-(1H-Imidazole-4-yl)-1-{(3-methoxy-benzyl)-[(2-phenyl-propylcarbamoyl)-methyl]-carbatnoyl)}-ethyl)-carbamic acid benzyl ester;

(S)-(2-(1H-Imidazole-4-yl)-1-{[(2-phenyl-propylcarbamoyl)-methyl]-[4-(pyridin-3-ylmethoxy)-benzyl]-carbamoyl}-ethyl)-carbamic acid benzyl ester;

(S)-(2-(1H-Imidazole-4-yl)-1-{naphthalen-1-ylmethyl-[(2-phenyl-propylcarbamoyl)-methyl]-carbamoyl}-ethyl)-carbamic acid benzyl ester;

(S)-{(2-(1H-Imidazole-4-yl)-1-[[(2-phenyl-propylcarbamoyl)-methyl]-(4-trifluoromethyl-benzyl)-carbamoyl]-ethyl}-carbamic acid benzyl ester;

(S)-(2-(1H-Imidazole-4-yl)-1-{[(2-methyl-2-phenyl-propylcarbamoyl)-methyl]-pyridin-3-ylmethyl-carbamoyl)}-ethyl)-carbamic acid benzyl ester;

(S)-(2-(1H-Imidazole-4-yl)-1-{[(2-methyl-2-phenyl-propylcarbamoyl)-methyl]-[4-(pyridin-2-ylmethoxy)-benzyl]-carbamoyl}-ethyl)-carbamic acid benzyl ester;

(S)-[1-(Benzyl-[(2-methyl-2-phenyl-propyl-carbamoyl)-methyl]-carbamoyl}-2-(1H-imidazole-4-yl)-ethyl]-carbamic acid benzyl ester;

(S)-(2-(1H-Imidazole-4-yl)-1-{(2-methyl-benzyl)-[(2-phenyl-propylcarbamoyl)-methyl]-carbamoyl}-ethyl)-carbamic acid benzyl ester;

(S)-(2-(1H-Imidazole-4-yl)-1-{(4-methoxy-benzyl)-[(2-methyl-2-phenyl-propylcarbamoyl)-methyl]-carbamoyl}-ethyl)-carbamic acid benzyl ester;

(S)-[1-{(4-Benzyloxy-benzyl)-[(2-cyano-2-phenyl-ethylcarbamoyl)-methyl]-carbamoyl)-2-(1H-imidazole-4-yl)-ethyl]-carbamic acid benzyl ester;

(S)-(2-(1H-Imidazole-4-yl)-1-{[(2-methyl-2-phenyl-propylcarbamoyl)-methyl]-pyridin-2-ylmethyl-carbamoyl}-ethyl)-carbamic acid benzyl ester;

(S)-(2-(1H-Imidazole-4-yl)-1-{(3-methyl-benzyl)-[(2-phenyl-propylcarbamoyl)-methyl]-carbamoyl}-ethyl)-carbamic acid benzyl ester;

(S)-[1-{(4-Dimethylamino-benzyl)-[(2-phenyl-propylcarbamoyl)-methyl]-carbamoyl}-2-(1H-imidazole-4-yl)-ethyl]-carbamic acid benzyl ester;

(S)-(2-(1H-Imidazole-4-yl)-1-{[(2-methyl-2-phenyl-propylcarbamoyl)-methyl]-[4-(pyridin-4-ylmethoxy)-benzyl]-carbamoyl}-ethyl)-carbamic acid benzyl ester;

(S)-(2-(1H-Imidazole-4-yl)-1-{[(2-methyl-2-phenyl-propylcarbamoyl)-methyl]-[4-(pyridin-3-ylmethoxy)-benzyl]-carbamoyl}-ethyl)-carbamic acid benzyl ester;

(2-(1-H-imidazole-4-yl)-1-{isobutyl-[(2-phenyl-propylcarbamoyl)-methyl]-carbamoyl)-ethyl)-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl)-carbamic acid benzyl ester;

(S)-2-(3-Benzyl-3-methyl-ureido)-N-(4-benzyloxy-benzyl)-3-(1H-imidazole-4-yl)-N-[(2-methyl-2-phenyl-propylcarbamoyl)-methyl]-propionamide;

(S)-1-[{(4-Benzyloxy-benzyl)-[(2-hydroxy-2-phenyl-ethylcarbamoyl)-methyl]-carbamoyl}-2-(3H-imidazole-4-yl)-ethyl)-carbamic acid benzyl ester;

(S)-(2-(1H-Imidazole-4-yl)-1-{(4-methoxy-benzyl)-[(2-phenyl-propylcarbamoyl)-methyl]-carbamoyl}-ethyl)-carbamic acid benzyl ester;

(S)-[1-((4-Benzyloxy-benzyl)-{[2-(2-chloro-phenyl)-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(1H-imidazole-4-yl)-ethyl]-carbamic acid thiophen-3-ylmethyl ester;

(S)-[1-{(4-Chloro-benzyl)-[1-(2-methyl-2-phenyl-propylcarbamoyl)-ethyl]-carbamoyl}-2-(3H-imidazole-4-yl)-ethyl]-carbamic acid benzyl ester;

(S)-(2-(1H-Imidazole-4-yl)-1-{(4-methyl-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{(2-methoxy-benzyl)-[(2-methyl-2-phenyl-propylcarbamoyl)-methyl]-carbamoyl}-ethyl)-carbamic acid benzyl ester;

(S)-2-(3-Benzyl-3-methyl-ureido)-N-(4-chloro-benzyl)-3-(1H-imidazole-4-yl)-N-[(2-methyl-2-phenyl-propylcarbamoyl)-methyl]-propionamide;

(S)-(2-(1H-Imidazole-4-yl)-1-{(3-methoxy-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{[2-methyl-2-phenyl-propylcarbamoyl)-methyl]-[2-(pyridin-4-ylmethoxy)-benzyl]-carbamoyl}-ethyl)-carbamic acid benzyl ester;

(S)-[1-{Cyclohexylmethyl-[(2-phenyl-propylcarbamoyl)-methyl]-carbamoyl}-2-(3H-imidazole-4-yl)-ethyl]-carbamic acid benzyl ester;

(S)-[1-{(4-Benzyloxy-benzyl)-[(2-phenyl-pentyl-carbamoyl)-methyl]-carbamoyl}-2-(3H-imidazole-4-yl)-ethyl]-carbamic acid benzyl ester;

(S)-[1-{[2-(4-Benzyloxy-phenyl)-ethyl]-[(2-methyl-2-phenyl-propylcarbamoyl)-methyl]-carbamoyl}-2-(3H-imidazole-4-yl)-ethyl3-carbamic acid benzyl ester;

(S)-(2-(3H-Imidazole-4-yl)-1-{[2-(4-methoxy-phenyl)-ethyl]-[(2-methyl-2-phenyl-propylcarbamoyl)-methyl]-carbamoyl}-ethyl)-carbamic acid benzyl ester;

(S)-[1-[{[2-(2-Amino-phenyl)-ethylcarbamoyl]-methyl}-(4-benzyloxy-benzyl)-carbamoyl]-2-(3H-imidazole-4-yl)-ethyl]-carbamic acid benzyl ester;

(2-(1H-imidazol-4-yl)-1-{isobutyl-[(2-phenyl-propylcarbamoyl)-methyl]-carbamoyl}-ethyl)-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-methyl-carbamic acid benzyl ester;

(S)-[1-{(4-Benzyloxy-benzyl)-[(2-methyl-2-phenyl-propylcarbamoyl)-methyl3-carbamoyl}-2-(3-methyl-3H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(1-methyl-1H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid furan-2-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid thiophen-2-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid pyridin-3-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid 1H-imidazole-4-ylmethyl ester;

(S)-2-(3-Benzyl-ureido)-N-(4-chloro-benzyl)-3-(3H-imidazole-4-yl)-N-[(2-methyl-2-phenyl-propylcarbamoyl)-methyl]-propionamide;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid 4-methoxy-benzyl ester;

(S)-2-(3-Benzyl-thioureido)-3-(3H-imidazole-4-yl)-N-(4-methyl-benzyl)-N-[(2-methyl-2-phenyl-propylcarbamoyl)-methyl]-propionamide;

(S)-2-Acetylamino-N-(4-benzyloxy-benzyl)-3-(3H-imidazole-4-yl)-N-[(2-methyl-2-phenyl-propylcarbamoyl)-methyl]-propionamide;

(S)-(2-(3H-Imidazole-4-yl)-1-{[(2-methyl-2-phenyl-propylcarbamoyl)-methyl]-pyridin-4-ylmethyl-carbamoyl}-ethyl)-carbamic acid benzyl ester;

(S)-{2-(3H-Imidazole-4-yl)-1-[(4-iodo-benzyl)-(phenethylcarbamoyl-methyl)-carbamoyl]-ethyl}-carbamic acid benzyl ester;

(S)-[1-{(4-Amino-benzyl)-[(2-methyl-2-phenyl-propylcarbamoyl)-methyl)-carbamoyl}-2-(3H-imidazole-4-yl)-ethyl]-carbamic acid benzyl ester;

(S)-[1-{(4-Ethoxy-benzyl)-[(2-methyl-2-phenyl-propylcarbamoyl)-methyl]-carbamoyl}-2-(3H-imidazole-4-yl)-ethyl]-carbamic acid benzyl ester;

(S)-[1-{[4-(2-Dimethylamino-ethoxy)-benzyl]-[(2-methyl-2-phenyl-propylcarbamoyl)-methyl]-carbamoyl}-2-(3H-imidazole-4-yl)-ethyl]-carbamic acid benzyl ester; and (2-(1H-Imidazol-4-yl)-1-{isobutyl-[(2-methyl-2-phenyl-propyl carbamoyl)-methyl]-carbamoyl}-ethyl)-carbamic acid benzyl ester.

DETAILED DESCRIPTION OF THE INVENTION

The present invention provides a compound having the Formula I

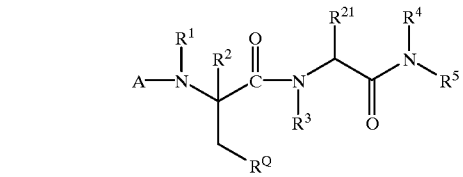

wherein $R^{21}$ is hydrogen or $C_1$–$C_6$ alkyl;

$R^Q$ is

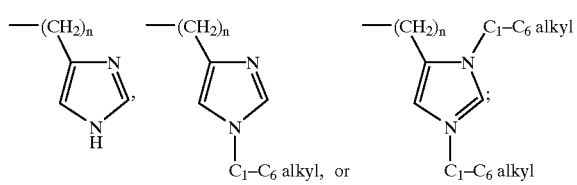

n is 0 or 1;

A is —$COR^a$, —$CO_2R^{a'}$, —$CONHR^{a'}$, —$CSR^a$, —$C(S)OR^{a'}$, —$C(S)NHR^{a'}$, —$SO_2R^a$, —$CONR^aR^{a''}$,

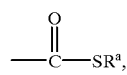

or

$R^a$, $R^{a'}$, and $R^{a''}$ are independently $C_1$–$C_6$ alkyl, —$(CH_2)_m$-cycloalkyl, —$(CH_2)_m$-aryl, —$(CH_2)_m$-heteroaryl;

each m is independently 0 to 3;

$R^1$, $R^2$, and $R^4$ are independently hydrogen or $C_1$–$C_6$ alkyl;

$R^3$ is

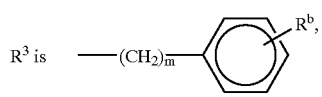

—$(CH_2)_m$-heteroaryl,

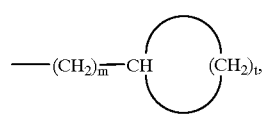

—$(CH_2)_m$-naphthyl, $C_1$–$C_6$ alkyl, or —$(CH_2)_m$-(heteroaryl substituted with $R^b$);

t is 2 to 6;

$R^b$ is —O-phenyl, —O-benzyl, halogen, $C_1$–$C_6$ alkyl, hydrogen, —$OC_1$–$C_6$ alkyl, —$NH_2$, —$NHR^a$, —$NR^aR^{a'}$,

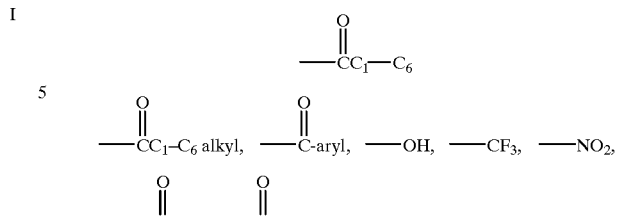

—O—$(CH_2)_y NR^aR^{a'}$, —O—$(CH_2)_m$-cycloalkyl, —$(CH_2)_m$-cycloalkyl, —O—$(CH_2)_m$-aryl, —$(CH_2)_m$-aryl, or —$(CH_2)_m$-heteroaryl;

y is 2 or 3;

$R^5$ is

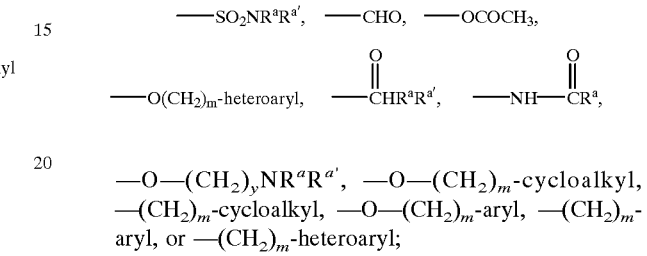

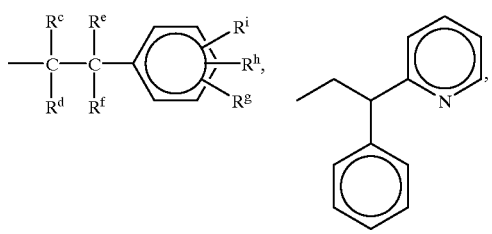

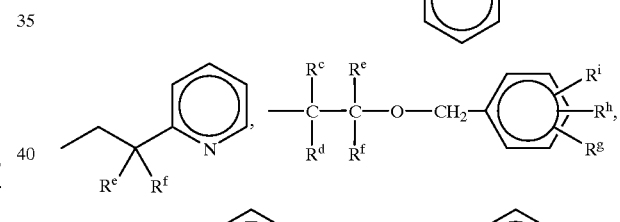

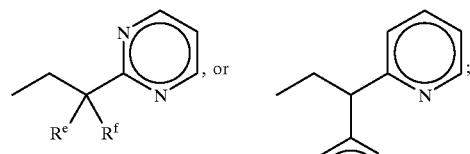

$R^i$, $R^g$, and $R^h$ are independently hydrogen, halogen, —$OC_1$–$C_6$ alkyl, $C_1$–$C_6$ alkyl, —CN, —$OPO_3H_2$, —$CH_2PO_3H_2$, —O-phenyl, —O-benzyl, —$NH_2$, $NHR^a$, —$NR^aR^{a'}$,

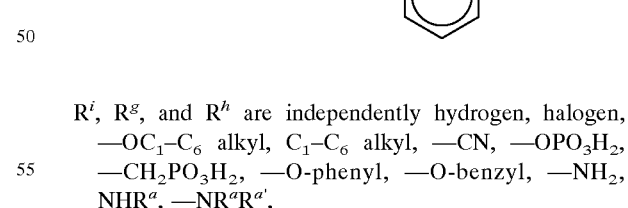

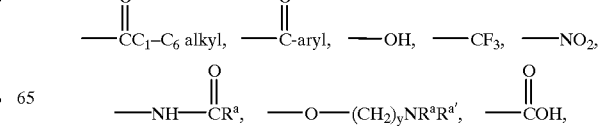

-continued

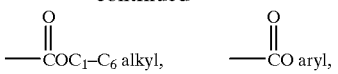

—N$_3$, —CF$_2$CF$_3$, SO$_2$R$^a$, —SO$_2$NR$^a$R$^{a'}$, —CHO, or —OCOCH$_3$; and R$^c$, R$^d$, R$^e$, and R$^f$ are independently C$_1$–C$_6$ alkyl, —(CH$_2$)$_m$-phenyl, hydrogen, —(CH$_2$)$_m$—OH, —(CH$_2$)$_m$NH$_2$, —(CH$_2$)$_m$-cycloalkyl, or —CN, and the pharmaceutically acceptable salts, esters, amides, and prodrugs thereof.

Also provided are compounds having the Formula II

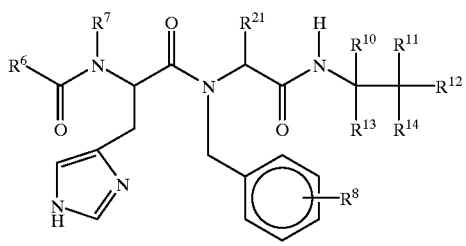

wherein

R$^6$ is —O-benzyl, —NH-benzyl, or

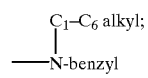

R$^{21}$ is hydrogen or methyl;

R$^7$ is hydrogen or methyl;

R$^8$ is hydrogen, halogen, C$_1$–C$_6$ alkyl, —O-benzyl, —OC$_1$–C$_6$ alkyl, —OF$_3$, —OH, —O—CH$_2$-pyridyl, or phenyl;

R$^{10}$, R$^{11}$, R$^{13}$, and R$^{14}$ are independently hydrogen, C$_1$–C$_6$ alkyl, or —(CH$_2$)$_m$-phenyl;

each m is independently 0 to 3;

R$^{12}$ is

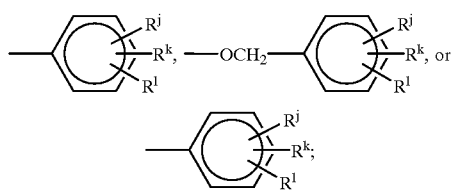

and

R$^j$, R$^k$, and R$^l$ are independently hydrogen, halogen, —OC$_1$–C$_6$ alkyl, —C$_1$–C$_6$ alkyl, or —NHR$^a$, or NH$_2$, and the pharmaceutically acceptable salts, esters, amides, and prodrugs thereof.

Also provided are compounds having the Formula III

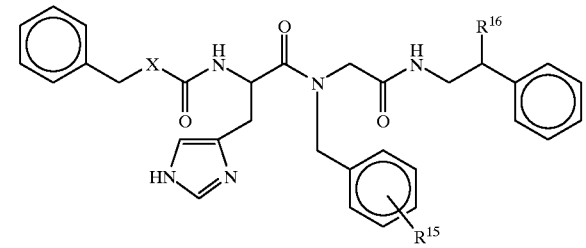

wherein

X is NH, O, or —N(CH$_3$);

R$^{15}$ is —O-benzyl, —CF$_3$, hydrogen, halogen, C$_1$–C$_6$ alkyl, —OC$_1$–C$_6$ alkyl, —O—CH$_2$)$_m$-pyridyli or phenyl;

m is 0 to 3; and

R$^{16}$ is a phenyl, hydrogen, or C$_1$–C$_6$ alkyl, and the pharmaceutically acceptable salts, esters, amides, and prodrugs thereof.

Also provided are compounds having the Formula IV

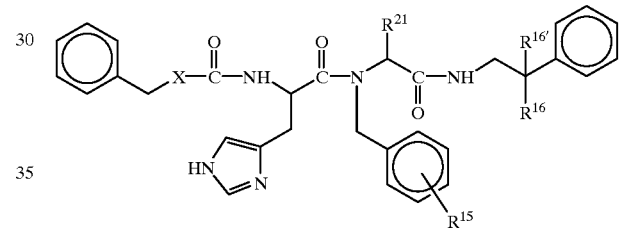

wherein

X is NH, O, or —N(CH$_3$);

R$^{15}$ is —O-benzyl, —CF$_3$, hydrogen, halogen, C$_1$–C$_6$ alkyl, —OC$_1$–C$_6$ alkyl, phenyl, or —OCH$_2$)$_m$-pyridyl;

R$^{16}$ and R$^{16'}$ are C$_1$–C$_6$ alkyl;

m is 0 to 3; and

R$^{21}$ is hydrogen or methyl, and the pharmaceutically acceptable salts, esters, amides, and prodrugs thereof.

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyll" means a saturated hydrocarbon ring which contains from 3 to 7 carbon atoms, for example, cyclopropyl, cyclobutyl, cyclopentyl, cyclohexyl, adamantyl, and the like.

The term "aryl" means an aromatic ring which is a phenyl, 5-fluorenyl, 1-naphthyl, or 2-naphthyl group, unsubstituted or substituted by 1 to 3 substituents selected from alkyl, O-alkyl and S-alkyl, OH, SH, F, Cl, Br, I, CF$_3$, NO$_2$, NH2, NHCH$_3$, N(CH$_3$)$_2$, NHCO-alkyl, (CH$_2$)$_m$CO$_2$H, (CH$_2$)$_m$CO$_2$-alkyl, (CH$_2$)HSO$_3$H, (CH$_2$)$_m$PO$_3$H$_2$, (CH$_2$)$_m$PO$_3$(alkyl)$_2$, (CH$_2$)$_m$SO$_2$NH$_2$ and (CH$_2$)$_m$SO$_2$NH-alkyl wherein alkyl is defined as above and m=0, 1, 2, or 3.

The term "heteroaryl" means a heteroaromatic ring which is a 2- or 3-thienyl, 2- or 3-furanyl, 2- or 3-pyrrolyl, 2-, 3-, or 4-pyridyl, imidazolyl, 2-, 3-, 4-, 5-, 6-, or 7-indoxyl group, unsubstituted or substituted by 1 or 2 substituents from the group of substituents described above for aryl. The symbol "—" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of a viral infection, restenosis, cancer, atherosclerosis, psoriasis, endometriosis, or prevents restenosis or atherosclerosis. A therapeutically effective amount of a compound of the present invention can be easily determined by one skilled in the art by administering a quantity of a compound to a patient and observing the result. In addition, those skilled in the art are familiar with identifying patients having cancer, viral infections, restenosis, atherosclerosis, psoriasis, or endometriosis or who are at risk of having restenosis or atherosclerosis.

The term "cancer" includes, but is not limited to, the following cancers:

breast;
ovary;
cervix;
prostate;
testis;
esophagus;
glioblastoma;
neuroblastoma;
stomach;
skin, keratoacanthoma;
lung, epidermoid carcinoma, large cell carcinoma, adenocarcinoma;
bone;
colon, adenocarcinoma, adenoma;
pancreas, adenocarcinoma;
thyroid, follicular carcinoma, undifferentiated carcinoma, papillary carcinoma;
seminoma;
melanoma;
sarcoma;
bladder carcinoma;
liver carcinoma and biliary passages;
kidney carcinoma;
myeloid disorders;
lymphoid disorders, Hodgkins, hairy cells;
buccal cavity and pharynx (oral), lip, tongue, mouth, pharynx;
small intestine;
colon-rectum, large intestine, rectum;
brain and central nervous system; and
leukemia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphtholate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylamnonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drua Design*, ed. Edward B. Roche, American Pharmaceutical Association and Pergamon Press, 1987, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), Cremophor EL (a derivative of castor oil and ethylene oxide; purchased from Sigma Chemical Co., St. Louis, Mo.) and suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar—agar, calcium carbonate, potato or tapioca starch, alginic acid, certain complex silicates, and sodium carbonate, (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, Cremophor EL (a derivative of castor oil and ethylene oxide; purchased from Sigma Chemical Co., St. Louis, Mo.), polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination go of optimum dosages for a particular patient is well known to those skilled in the art.

The compounds of the present invention can exist in different stereoisomeric forms by virtue of the presence of asymmetric centers in the compounds, It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification or the claims in any way.

Scheme 1 shows a general method by which the compounds of the present invention can be prepared, by illustrating the synthesis of [1-[(4-benzyloxy-benzyl)-(phenethyl-carbamoyl-methyl)-carbamoyl]-2-(3H-imidazole-4-yl)-ethyl]-carbamic acid benzyl ester (Example 2). Reductive amination of 4-benzyloxybenzaldehyde with glycine methyl ester hydrochloride was carried out in methylene chloride with sodium triacetoxyborohydride. The (4-benzyloxybenzylamino)acetic acid methyl ester was then coupled to Cbz-His in dimethylformamide with 1-hydroxybenzotriazole (HOBt) and dicyclohexylcarbodiimide (DCC) as coupling agents. The resulting product was saponified using lithium hydroxide at 0° C., followed by coupling with phenethylamine hydrochloride in dimethylformamide, with HOBt and DCC as coupling agents, and in the presence of triethylamine.

The following abbreviations are used herein:

| Abbreviations | |
|---|---|
| Cbz or Z | Carbobenzoxy |
| His | Histidine |
| Trt | trityl |
| TEA | Triethylamine |
| HOAc | Acetic acid |
| Et$_2$O | Diethylether |
| tBu | tert-Butyl |
| TFA | Trifluoroacetic acid |
| ES-MS | Electrospray Mass Spectrometry |
| FAB-MS | Fast Atom Bombardment Mass Spectrometry |
| HOBt | 1-Hydroxybenzotriazole |
| DCC | Dicyclohexylcarbodiimide |
| THF | Tetrahydrofuran |
| PyBOP | Benzotriazole-1-yl-oxy-tris-pyrrolidino-phosphonium hexafluorophosphate |
| DIEA | Diisopropylethylamine |
| DMF | Dimethylformamide |
| Et$_3$N | Triethylamine |
| OAc | Acetate |
| Et$_2$O | Diethyl ether |
| Boc | tert-Butoxycarbonyl |
| iBuOCOCl | Isobutylchloroformate |
| NMM | N-methylmorpholine |
| DMSO | Dimethylsulfoxide |

SCHEME 1

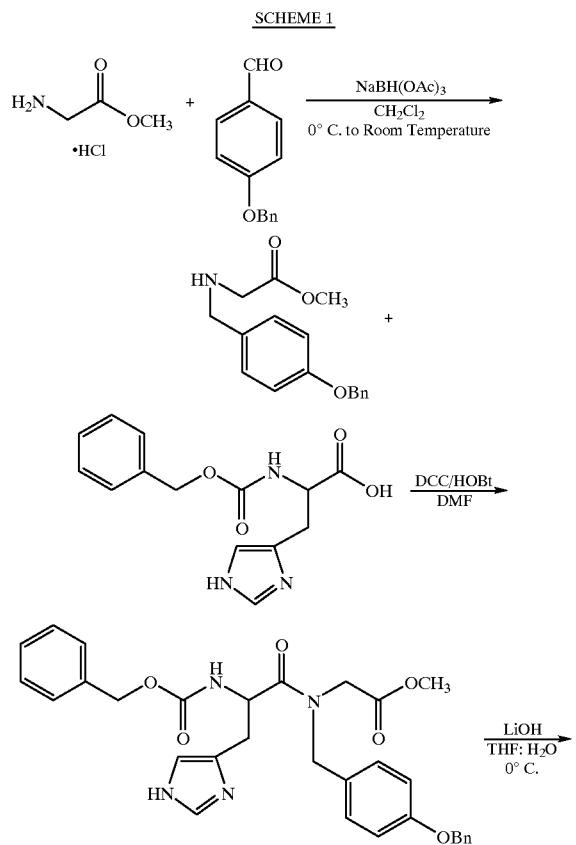

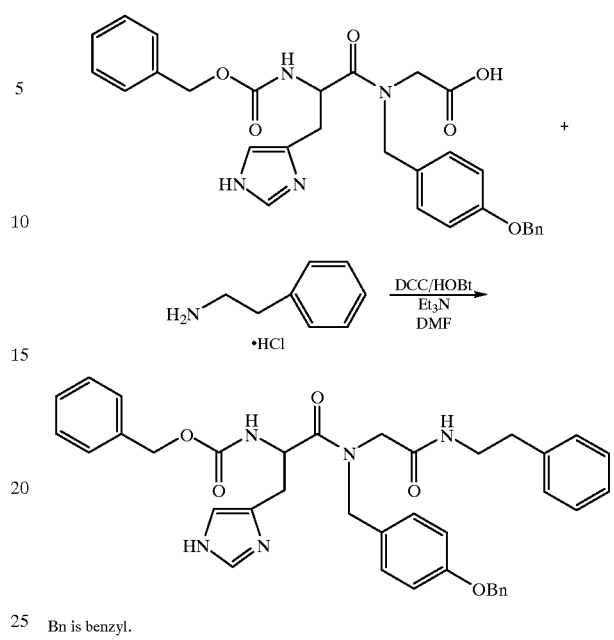

Bn is benzyl.

Scheme 2 shows a method by which compounds of the present invention can be prepared, by illustrating the synthesis of Example 15, (1-{(4-benzyloxy-benzyl)-[(2-methyl-2-phenyl-propylcarbamoyl)-methyl]-carbamoyl}-2-(3H-imidazole-4-yl)-ethyl]-carbamic acid benzyl ester. Reductive amination of 4-benzyloxy-benzaldehyde with glycine methyl ester was carried out in methylene chloride with sodium triacetoxyborohydride. The (4-benzyloxybenzylamino) acetic acid methyl ester was then coupled to Cbz-His-(trityl) in methylene chloride with benzotriazole-1-yl-oxy-tris-pyrrolidino-phosphonium hexafluorophosphate (PYBOP) as coupling agent in the presence of diisopropylethylamine (DIEA) as the base. The resulting product was saponified using lithium hydroxide at 0° C., followed by coupling with β,β-dimethylphenethylamine hydrochloride in methylene chloride, with 1-hydroxybenzotriazole (HOBt) and dicyclohexylcarbodiimide (DCC) as coupling agents, and triethylamine. The trityl group was removed in the presence of acetic acid in water, at reflux. The β,β-dimethylphenethylamine hydrochloride was prepared from benzyl cyanide, which was treated with 2 equivalents of sodium hydride in tetrahydrofuran (THF) and 2 equivalents of methyl iodide in THF followed by hydrogenation (H$_2$, Pd/C, ammonia) and treatment with HCl to give the HCl salt.

SCHEME 2

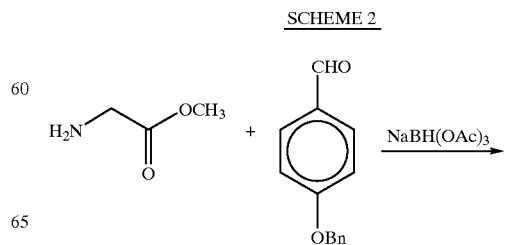

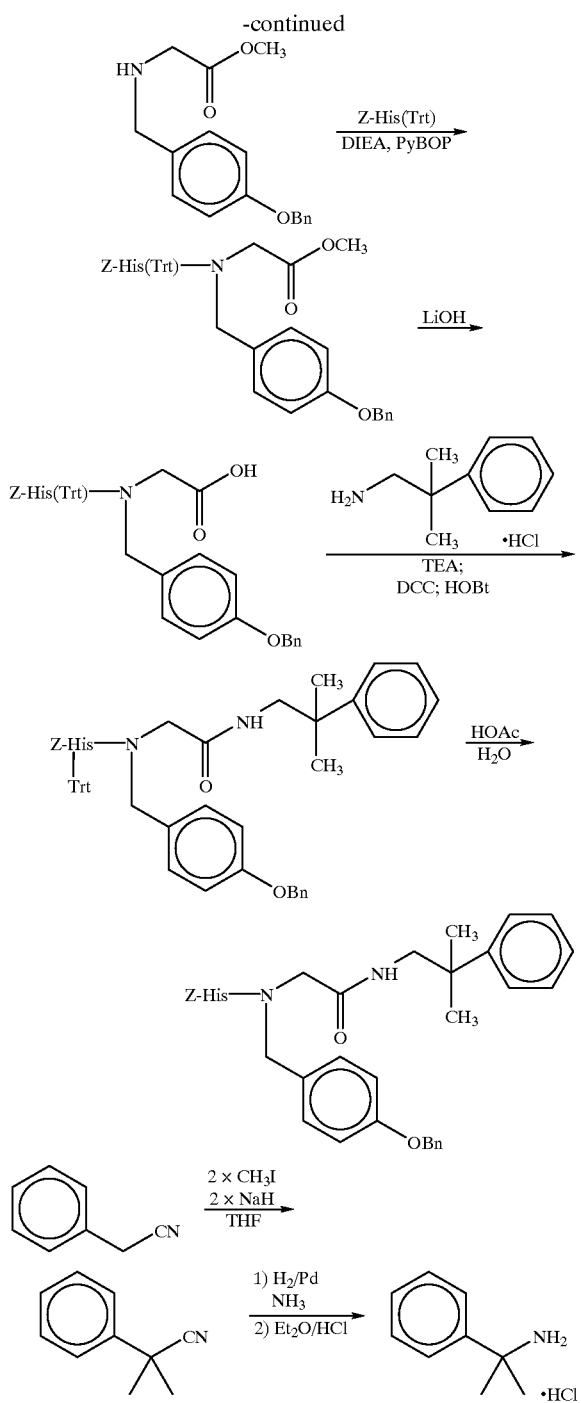

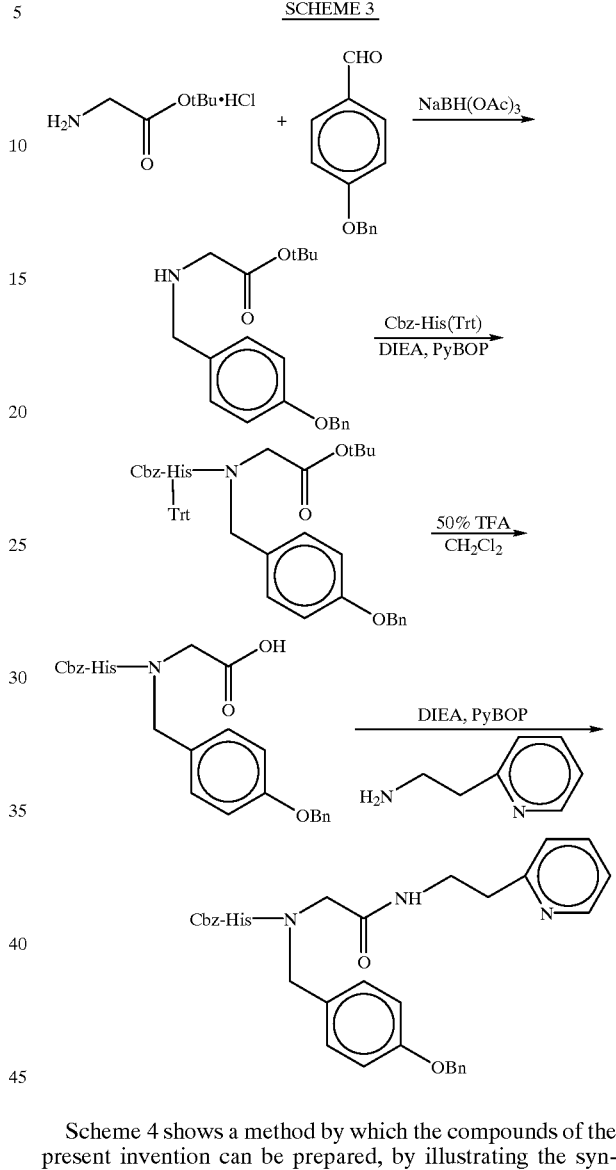

2-pyridineethaneamine in methylene chloride was carried out with PyBOP as coupling agent, and diisopropylethylamine as the base.

Scheme 3 shows a method by which the compounds of the present invention can be prepared, by illustrating the synthesis of Example 8, [1-{(4-Benzyloxy-benzyl)-[(2-pyridin-2-yl-ethyl-carbamoyl)-methyl)-carbamoyl)-2-(1H-imidazole-4-yl)-ethyl]-carbamic acid benzyl ester. Reductive amination of 4-benzyloxy benzaldehyde with glycine t-butyl ester was carried out in methylene chloride with sodium triacetoxyborohydride. The (4-benzyloxybenzylamino)acetic acid t-butyl ester was then coupled to Cbz-histidine-(trityl) in methylene chloride with PyBOP as coupling agent and DIEA as the base. The resulting product was deprotected by treatment with 50% trifluoroacetic acid in methylene chloride. Coupling with Scheme 4 shows a method by which the compounds of the present invention can be prepared, by illustrating the synthesis of Example 7, [1-((4-Benzyloxy-benzyl)-{[2-(2-fluoro-phenyl)-ethylcarbamoyl]-methyl)-carbamoyl)-2-(1H-imidazole-4-yl)-ethyl]-carbamic acid benzyl ester. Boc-glycine was coupled to 2-fluoro-phenethylamine in tetrahydrofuran (THF) in the presence of isobutylchloroformate as coupling agent and N-methylmorpholine as the base. The Boc group was then removed by treatment with 50% TFA in methylene chloride for 30 minutes. Reductive amination of 4-benzyloxy-benzaldehyde with N-[2-(2-fluorophenyl)-ethyl]-glycinamide TFA salt was carried out in methylene chloride with sodium triacetoxyborohydride and potassium acetate as the base. The N-[2-(2-fluorophenyl)-ethyl]-N$^\alpha$-(4-benzyloxy-benzyl)-glycinamide.HCl was then coupled to Cbz-histidine-(trityl) in methylene chloride with benzotriazole-1-yl-oxy-tris-pyrrolidino-phosphonium hexafluorophosphate (PyBOP) as coupling agent and diisopropylethylamine as the base. The resulting product was deprotected by treatment with 50% trifluoroacetic acid in methylene chloride, with trisopropylsilane as the scavenger.

SCHEME 4

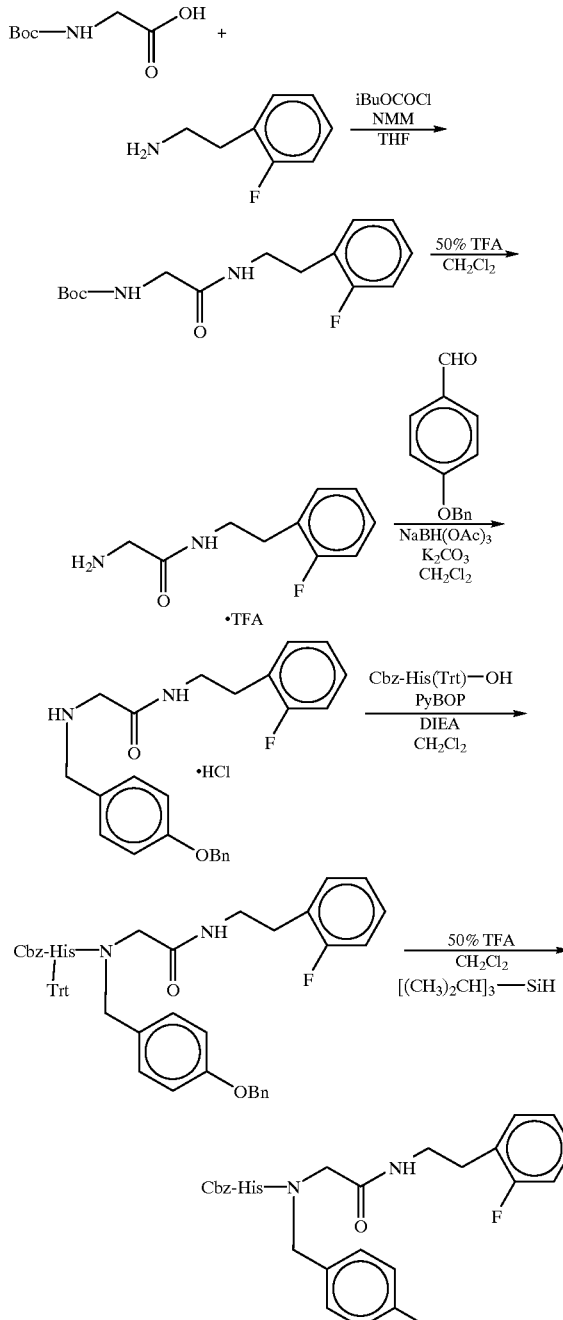

Scheme 5 shows a method by which the compounds of the present invention can be prepared, by illustrating the synthesis of Example 62, (2-(1H-imidazol-4-yl)-1-(isobutyl-[(2-phenyl-propylcarbamoyl)-methyl]-carbamoyl}-ethyl)-carbamic acid benzyl ester. Boc-glycine was coupled to β-methylphenethylamine in methylene chloride, in the presence of dicyclohexylcarbodiimide (DCC) and 1-hydroxybenzotriazole (HOBt) as coupling agents and diisopropylethylamine as the base. The boc group was then removed by treatment with 30% TFA in methylene chloride for 2 hours and reductive amination of isobutyraldehyde in methylene chloride with sodium triacetoxyborohydride and sodium acetate as the base was carried out. The above product was then coupled to Cbz-histidine-(trityl) in methylene chloride with O-(7-azabenzotriazol-1-yl)-N,N,N',N'-tetramethyluronium hexafluorophosphate (HATU) and 1-hydroxy-7-azabenzotriazole(HOAt) as coupling agents and diisopropylethylamine as the base. The resulting product was deprotected by treatment with 50% trifluoroacetic acid in methylene chloride.

SCHEME 5

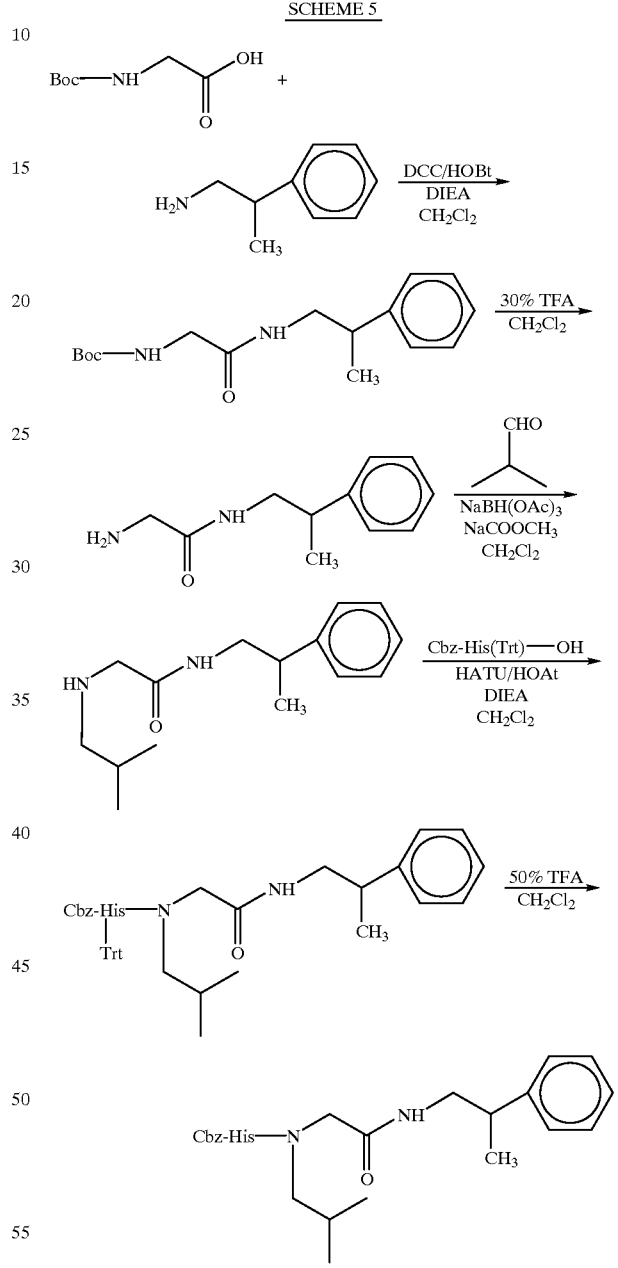

EXAMPLE 1

(S)-N-[(Phenylmethoxy)carbonyl]-L-histidyl-N-[2-(phenylmethoxy)ethyl]-$N^2$-[[4-(phenylmethoxy)phenyl]-methyl]alycinamide Step 1: (4-Benzyloxybenzylamino)acetic Acid Methyl Ester To a mixture of glycine methyl ester hydrochloride (2.07 g, 16.5 mmol) and 4-benzyloxybenzaldehyde (3.18 g, 15.0 mmol) in CH$_2$Cl$_2$ (50 mL) at 0° C. was added sodium triacetoxyborohydride (3.81 g, 18.0 mmol). The mixture was allowed to warm to room temperature and stirred for 4 hours. Aqueous NaHCO$_3$ was added, and the mixture was stirred for 30 minutes. The aqueous layer was extracted three times with CH$_2$Cl$_2$. The combined organic extracts were washed with brine, dried over MgSo$_4$, and concentrated. Flash chromatography (75% ethyl acetate/hexane) gave 1.98 g (46%) of the title compound as a white solid; mp 57–58° C.

Step 2: N-[N-[(Phenylmethoxy)carbonyl]-L-histidyl]-N-[[4-(phenylmethoxy)phenyl]methyl]calycine Methyl Ester To a suspension of CBZ-histidine (1.22 g, 4.21 mmol) in DMF (dimethylformamide) (10 mL) was added HOBT (hydroxybenzotriazole) hydrate (0.77 g, 5.05 mmol) and DCC (dicyclohexylcarbodiimide) (1.04 g, 5.05 mmol). The amine from Step I above (1.20 g, 4.21 mmol) was then added, and the mixture was stirred at room temperature overnight. The mixture was filtered, and the filtrate was diluted with CHCl$_3$, washed twice with saturated NaHCO$_3$, brine, dried over MgSO$_4$, and concentrated. Flash chromatography gave 1.68 g (72%) of the title compound as a white foam; ES-MS (electrospray mass spectrometry) 557 (m +1).

Step 3: N-[N-[(Phenylmethoxy)carbonyl]-L-histidyl]-N-[[4-(phenylmethoxy)phenyl]methyl]glycine To a solution of the ester from Step 2 (1.53 g, 2.75 nmol) in THF (tetrahydrofuran) (15 mL) and H$_2$O (5 mL) at 0° C. was added LiOH hydrate (0.14 g, 3.30 mmol), and the solution was stirred 5 hours at 0° C. The solution was concentrated, the residue taken up in H$_2$O, and the pH adjusted to 4–5 with 1N HCl. The resulting mixture was concentrated and dried in vacuo to afford 1.65 g of the title compound as a white solid; FAB-MS 543 (m+1).

Analysis calculated for C$_{30}$H$_{30}$N$_4$O$_6$.1.2 LiCl.2.0 H$_2$O: C, 57.24; H, 5.44; N, 8.90. Found: C, 57.35; H, 5.32; N, 8.62.

Step 4: (S)-N-[(Phenylmethoxy)carbonyl]-L-histidyl-N-[2-(phenylmethoxy)-ethyl]-N$^2$-[[4-(phenylmethoxy)phenyl]methyl]-glycinamide To a solution of the acid from Step 3 (2.9 g, 5.33 mmol) in DMF (15 mL) was added HOBt hydrate (0.98 g, 6.39 mmol) and DCC (1.32 g, 6.39 mmol) followed by 2-benzyloxyethylamine hydrochloride (1.0 g, 5.33 nmmol). Et$_3$N (triethylamine) (0.82 mL, 5.86 mmol) was added, and the mixture was stirred overnight at room temperature. The mixture was filtered, and the filtrate was diluted with CHCl$_3$, washed twice with saturated NaHCO$_3$, brine, dried over MgSO$_4$, and concentrated. Flash chromatography (2–5% Methanol/CHCl$_3$) gave 2.25 g (63%) of the title compound as a white foam; ES-MS 676 (m+1).

EXAMPLE 2

(S)-[1-[(4-Benzyloxy-benzyl)-(phenethyl-carbamoyl-methyl)-carbamoyl]-2-(3H-imidazole-4-yl)-ethyl]-carbamic Acid Benzyl Ester (S)-[1-[(4-Benzyloxy-benzyl)-(phenethyl-carbamoyl-methyl)-carbamoyl]-2-(3H-imidazole-4-yl)-ethyl]-carbamic acid benzyl ester can be made according to Example 1, Step 4, by substituting phenethylamine for 2-benzyloxyethylamine hydrochloride. The title compound is obtained as a while solid; ES-MS 646 (m+1).

EXAMPLE 3

(S)-[1-[[2-Benzyloxy-ethylcarbamoyl]-methyl]-[4-chlorobenzyl]-carbamoyl]-2-(1H-imidazole-4-yl)-ethyl]-carbamic Acid Benzyl Ester (S)-[1-[[2-Benzyloxy-ethylcarbamoyl]-methyl]-[4-chlorobenzyl]-carbamoyl]-2-(1H-imidazole-4-yl)-ethyl]-carbamic acid benzyl ester can be made according to Example 1, Step 1, by substituting 4-chlorobenzaldehyde for 4-benxyloxybenzaldehyde. The title compound is obtained as a white solid; ES-MS 604 (m+1).

EXAMPLE 4

(S)-[1-[(4-Benzyloxy-benzyl)-[(2-phenyl-propyl-carbamoyl)-methyl]-carbamoyl]-2-(1H-imidazole-4-yl)-ethyl]carbamic Acid Benzyl Ester (S)-[1-[(4-Benzyloxy-benzyl)-[(2-phenyl-propyl-carbamoyl)-methyl]-carbamoyl]-2-(1H-imidazole-4-yl)-ethyl]carbamic acid benzyl ester can be prepared according to Example 1, Step 4, by substituting β-methylphenethylamine for 2-benzyloxyethylamine hydrochloride. The title compound was obtained as a white solid; ES-MS 660 (m+1).

EXAMPLE 5

(S)-[1-[(4-Benzyloxy-benzyl)-[(2,2-diphenyl-ethylcarbamoyl)-methyl]-carbamoyl]-2-(1H-imidazole-4-yl)-ethvl]-carbamic Acid Benzyl Ester (S)-[1-[(4-Benzyloxy-benzyl)-[(2,2-diphenyl-ethylcarbamoyl)-methyl]-carbamoyl]-2-(1H-imidazole-4-yl)-ethyl]-carbamic acid benzyl ester can be prepared according to Example 1, Step 4, by substituting 2,2-diphenylethylamine for 2-benzyloxyethylamine hydrochloride. The title compound was obtained as a white powder; ES-MS 722 (m+1).

EXAMPLE 6

(S)-N-(4-Benzyloxy-benzyl)-2-(3-benzyl-ureido)-3-(1H-imidazole-4-yl)-N-[(2-phenyl-propylcarbamoyl)-methyl]-propionamide The title compound can be prepared according to Example 1, Step 2, by substituting benzyl-urea-histidine (Steps 1 and 2) for Cbz-histidine. The title compound is obtained as a white solid; ES-MS 659 (m+1).

Step 1: Benzyl-urea-histidine Methyl Ester

To a solution of histidine methyl ester hydrochloride (2.0 g, 4.3 mmol) in methylene chloride, at 0° C., was added benzyl isocyanate (0.58 mL, 0.63 g, 4.7 nmol) and triethylamine (1.32 mL, 9.5 mmol), and the solution was stirred overnight at room temperature. The solution was concentrated and the residue taken up in ethyl acetate. The solution was washed with water, saturated NaHCO$_3$, brine, dried over MgSO$_4$, and concentrated. The product was obtained as a white foam (1.09 g, 84%).

Step 2: Benzyl-urea-histidine

To a solution of the ester from Step 1 (1.9 g, 3.5 mmol) in THF:methanol (10 mL each) and water (2 mL) was added sodium hydroxide (0.4 g, 10 mmol), and the solution was stirred overnight at room temperature. The solution was added to 1N HCl:ethyl acetate (30 mL each). The organic layer was separated and washed with 1N HC1, brine, dried over MgSO$_4$, and concentrated. The product was obtained as a white foam (0.53 g, 53%); ES-MS 289 (m+1).

EXAMPLE 6a (S)-N-(4-Benzvloxy-benzyl)-2-(3-benzyl-ureido)-3-(1H-imidazole-4-yl)-N-[(2-phenyl-propylcarbamoyl)-methyl]-priopionamide The title compound can be prepared according to Example 1, Step 2, by substituting benzyl-urea-histidine- (trityl) (Steps 1 and 2) for Cbz-histidine and Step 4, by substituting β-methylphenethylamine for 2-benzyloxyethylamine hydrochloride. The title compound is obtained as a white solid; ES-MS 659 (m+1).

Step 1: Benzyl-urea-histidine-trityl Methyl Ester

To a solution of histidine-trityl methyl ester hydrochloride (2.0 g, 4.3 mmol) in methylene chloride, at 0° C., was added benzyl isocyanate (0.58 mL, 0.63 g, 4.7 mmol) and triethylamine (1.32 mL, 9.5 mmol), and the solution was stirred overnight at room temperature. The solution was concentrated and the residue taken up in ethyl acetate. The solution was washed with water, saturated NaHCO$_3$, brine, dried over MgSO$_4$, and concentrated. The product was obtained as a white foam (1.95 g, 83%).

Step 2: Benzyl-urea-histidine-(trityl).HCl

To a solution of the ester from Step 1 (1.9 g, 3.5 mmol) in THF:methanol (10 mL each) and water (2 mL) was added sodium hydroxide (0.4 g, 10 mmol), and the solution was stirred overnight at room temperature. The solution was added to 1N aqueous HCl:ethyl acetate (30 mL each). The organic layer was separated and washed with 1N HCl$_1$, brine, dried over MgSO$_4$, and concentrated. The product was obtained as a white foam (1.0 g, 53%); ES-MS 531 (m+1).

EXAMPLE 7

(S)-[1-((4-Benzyloxy-benzyl)-{[2-(2-fluoro-phenyl)-ethylcarbamoyl]-methyl}-carbamoyl)-2-(1H-imidazole-4-yl)-ethyl]-carbamic Acid Benzyl Ester Step 1: N$^\alpha$-Boc-N-[2-(2-fluororphenyl)-ethyl]-glycinamide To a solution of Boc-glycine (1.75 g, 10 mmol) in THF (50 mL) at 0° C. was added isobutylchloroformate (1.3 mL, 10 mmol), followed by N-methylmorpholine (1.1 mL, 10 mmol). The resulting suspension was stirred for 5 minutes at 0° C., then treated with 2-[(2-fluorophenyl)-ethyl]-amine (10 mmol). The suspension was stirred at room temperature overnight. The reaction was treated with 1N HCl and was extracted with diethyl ether (2×50 mL). The organic extracts were combined, washed successively with water, a saturated aqueous NaHCO$_3$ solution, and then water. The organic extracts were dried over MgSO$_4$ and concentrated. Flash chromatography (5% methanol in methylene chloride) gave 1.93 g (65%) of the title compound as a white solid; CI-MS 297 (m+1).

Step 2: N-[2-(2-Fluorophenyl)-ethyl]-glycinamide Trifluoroacetic Acid Salt

To a solution of the compound from Step 1 above (1.92 g, 6.48 mmol) in methylene chloride (20 mL) was added trifluoroacetic acid (20 mL). The solution was stirred for 30 minutes, then concentrated. The residue was dissolved in methylene chloride and reconcentrated to give the title compound as an oil. This was used in the next reaction without characterization.

Step 3: N-[2-(2-Fluorohenyl)-ethyl]-Nα-(4-benzyloxy-benzyl)-glycinamide Hydrochloric Salt To a suspension of the compound from Step 2 above (6.48 mmol), 4-benzyloxybenzaldehyde (1.38 g, 6.48 mmol) and potassium acetate (1.27 g, 12.96 mmol) in methylene chloride (50 mL), cooled to 0° C., was added sodium triacetoxyborohydride (1.79 g, 8.43 mmol). The reaction was allowed to warm to room temperature and was stirred for 3 hours. The reaction was treated with a saturated aqueous NaHCO$_3$ solution, and the layers were separated. The aqueous layer was extracted with methylene chloride (2×20 mL). The organic layers were combined and concentrated. The residue was dissolved in diethyl ether and treated with 1N HCl (8 mL). The precipitate was collected by filtration to give 1.46 g (52.6%) of the title compound as an off-white solid; CI-MS 393 (m+1).

Step 4: [1-((Benzyloxy-benzyl)-{[2-(2-fluorophenyl)-ethyl-carbamoyl]-methyl}-carbamoyl)-2-(1-trityl-1H-imidazole-4-yl)-ethyl]-carbamic Acid Benzyl Ester To a solution of (S)-(2-benzyloxycarbonylamino-3-(1-trityl)-1H-imidazole-4-yl)-propionic acid (Cbz-histidine-(trityl)) (Hudspeth J. P., Kaltenbronn J. S., Repine J. T., Roark W. H., Stier M. A., Renin Inhibitors III, U.S. Pat. No. 4,735,933; 1988) (0.532 g, 1.0 mmol) in methylene chloride (20 mL) was added diisopropylethylamine (0.48 mL, 2.75 mmol) and benzotriazole-1-yl-oxy-tris-pyrrolidino-phosphonium hexafluorophosphate (0.520 g, 1.0 mmol). The mixture was then treated with the amine hydrochloride salt (0.429 g, 1.0 mmol) from Step 3 above and stirred for 4 hours. The reaction was treated with a saturated aqueous NaHCO$_3$ solution, and the layers were separated. The aqueous layer was extracted with methylene chloride (2×30 mL). The organic layers were combined, dried over MgSO$_4$, and concentrated. Flash chromatography (2% methanol in methylene chloride) gave 0.501 g (55%) of the title compound as a white foam; ES-MS 906.5 (m+1).

Step 5: [1-((4-Benzyloxy-benzyl)-{[2-(2-fluoro-phenyl)-ethylcarbamoyl]-methyl}-carbamoyl)-2-(1H-imidazole-4-yl)-ethyl]-carbamic Acid Benzyl Ester To a solution of the trityl compound (0.49 g, 0.54 mmol) from Step 4 above in methylene chloride (5 mL) was added TFA (5 mL) and triisopropylsilane (0.25 mL). The solution was stirred for 3 hours, then concentrated. The residue was partitioned between a saturated aqueous solution of NaHCO$_3$ and ethyl acetate. The layers were separated and the aqueous layer was extracted with ethyl acetate (2×20 mL). The organic layers were combined, dried over MgSO$_4$, and concentrated. Flash chromatography (10% methanol in methylene chloride) gave 0.248 g (37%) of the title compound as a white foam; ES-MS 664.4 (m+1).

EXAMPLE 8

(S)-[1-{(4-Benzyloxy-benzyl)-[(2-pyridin-2-yl-ethylcarbamoyl)-methyl]-carbamoyl}-2-(1H-imidazole-4-yl)-ethyl]-carbamic Acid Benzyl Ester Step 1: (4-Benzyloxybenzylamino) Acetic Acid t-butyl Ester To a mixture of glycine t-butyl ester hydrochloride (0.84 g, 5 mmol), and 4-benzyloxy-benzaldehyde (0.53 g, 2.5 mmol) in CH$_2$Cl$_2$ (25 mL) at 0° C. was added sodium triacetoxyborohydride (0.81 g, 3.8 mmol). The mixture was allowed to warm to room temperature and stirred overnight. Aqueous NaHCO$_3$ was added, and the mixture was stirred for 30 minutes. The aqueous layer was extracted 3 times with CH$_2$Cl$_2$. The combined organic extracts were washed with brine, dried over MgSO$_4$, and concentrated. Flash chromatography (ethyl acetate) gave 0.38 g (59%) of the title compound as a white solid.

Step 2: N-[N-[(Phenylmethoxy)carbonyl]-L-histidyl-trityl]-N-[[4-(phenylmethoxy)phenyl]methyl]-glycine t-butyl Ester To a suspension of Cbz-histidine-(trityl) (0.89 g, 1.7 mmol) in methylene chloride (25 mL) was added PyBOP (2.63 g, 5.05 mmol) and diisopropylethylamine (0.68 mL, 3.9 mmol). The amine from Step 1 above (0.38 g, 1.5 mmol) was then added, and the mixture was stirred at room temperature overnight. The reaction mixture was concentrated in vacuo, the residue taken up in ethyl acetate, which was washed 3 times with saturated NaHCO$_3$, brine, dried over MgSO$_4$, and concentrated. Flash chromatography gave 0.59 g (51%) of the title compound as a white foam; ES-MS 841 (m+1).

Step 3: N-[N-[(Phenylmethoxy)carbonyl]-L-histidyl]-N-[[4-(phenylmethoxy)phenyl]methyl]glycine To a solution of the ester from Step 2 (0.59 g, 0.76 mmol), 50% trifluoroacetic acid in methylene chloride (25 mL) was added. The reaction was stirred at room temperature for 3 hours. The solution was concentrated in vacuo. Cold diethyl ether was added to the residue, and the solution was left at 4° C. overnight. A white precipitate was obtained, filtered, and dried; 0.33 g (80%).

Step 4: [1-{(4-Benzyloxy-benzyl)-[(2-pyridin-2-yl-ethylcarbamoyl)-methyl]-carbamoyl}-2-(1H-imidazole-4-yl)-ethyl]-carbamic Acid Benzyl Ester To a solution of the acid from Step 3 (0.33 g, 0.61 mmol) in methylene chloride was added PyBOP (0.67 g, 1.3 mmol) and diisopropylethylamine (0.23 mL, 1.3 mmol) followed by 2-pyridineethaneamine hydrochloride (0.082 g, 0.67 mmol). The mixture was stirred overnight at room temperature. The reaction mixture was concentrated in vacuo, the residue taken up in ethyl acetate, which was washed 3 times with saturated $NaHCO_3$, brine, dried over $MgSO_4$, and concentrated. Flash chromatography gave 0.156 g (37%) of the title compound as a white foam; ES-MS 647 (m+1).

EXAMPLE 9

(S)-[1-((4-Benzyloxy-benzyl)-{[2-(2-bromo-phenyl)-ethylcarbamoyl]-methyl}-carbamoyl)-2-(1H-imidazole-4-yl)-ethyl]-carbamic Acid Benzyl Ester The title compound can be prepared according to Example 8, Step 4, by substituting 2-bromo-phenethylamine (Steps 1 and 2) for 2-pyridineethane-amine.HCl. The title compound is obtained as a white foam (10%); ES-MS 725 (m+1).

Step 1: o-Bromo-nitrostyrene

To a solution of o-bromo-benzaldehyde (4 g, 21.6 mmol) and nitromethane (1.32 g, 21.6 mmol) in methanol (5 mL) was added NaOH (0.908 g, 22.7 nmol) in 1 mL of $H_2O$. After 45 minutes, the precipitate was dissolved in 10 mL of $H_2O$. The product precipitated out after the addition of 6N HCl. The product was recrystallized from ethanol; 0.312 g (6%).

Step 2: 2-Bromo Phenethylamine

To the styrene of Step 1 (0.310 g, 1.3 mmol) in 5 mL of THF was added 1 M $LiAlH_4$ solution in THF (5.2 mL, 5.2 mmol) at 0° C. The solution was stirred for 1 hour. A concentrated $KHSO_4$ solution was added dropwise to destroy the excess of $LiAlH_4$. The solution was filtered over celite and the filtrate concentrated in vacuo to give a yellow oil; 150 mg (58%).

EXAMPLE 10

(S)-1-{(4-Benzyloxy-benzyl)-[(R)-(1-methyl-2-phenyl-ethylcarbamoyl)-methyl]-carbamoyl}-2-(1H-imidazole-4-vl)-ethyl]-carbamic Acid Benzyl Ester The title compound can be prepared according to Example 15, Step 5, by substituting L-amphetamine for β,β-dimethylphenethylamine hydrochloride. The title compound is obtained as a white foam (90%); ES-MS 660 (m+1).

EXAMPLE 11

(S)-1-{(4-Benzyloxy-benzyl)-[(S)-(1-methyl-2-phenyl-ethylcarbamoyl)-methyl]-carbamoyl}-2-(1H-imidazole-4-yl)-ethyl]-carbamic Acid Benzyl Ester The title compound can be prepared according to Example 15, Step 5, by substituting D-amphetamine for β,β-dimethylphenethylamine hydrochloride. The title compound is obtained as a white foam; ES-MS 660 (m+1).

EXAMPLE 12

(S)-[1-{(4-Benzyloxy-benzyl)-[(2-phenyl-2-pyridin-2-yl-ethylcarbamoyl)-methyl]-carbamoyl}-2-(1H-imidazole-4-yl)-ethyl]-carbamic Acid Benzyl Ester The title compound can be prepared according to Example 8, Step 4, by substituting 2-[α-(aminomethyl)-benzyl]pyridine hydrochloride (Step 1) for 2-pyridineethane-amineHCl. The title compound is obtained as a white foam (64%); ES-MS 723 (m+1).

Step 1: 2-[α(Aminomethyl)benzyl]pyridine Hydrochloride

α-(2-Pyridyl)-phenylacetonitrile (97.1 g, 0.5 mol) was reduced with Raney cobalt (25 g) and triethylamine (25 mL) in toluene (500 mL). The solution was filtered, and the filtrate was concentrated. The residue was dissolved in diethyl ether, and HCl was bubbled in. The hydrochloride salt precipitated out of the solution.

EXAMPLE 13

(S)-[1-{(4-Chloro-benzyl)-[(2-phenyl-propylcarbamoyl)-methyl]-carbamoyl}-2-(1H-imidazole-4-yl)-ethyl]-carbamic Acid Benzyl Ester The title compound can be prepared according to Example 8, Step 4, by substituting β-methyl-phenethylamine for 2-pyridineethane-amine.HCl and in Step 1, by substituting p-chloro-benzaldehyde for 4-benzyloxy-benzaldehyde. The title compound is obtained as a white foam (17%); ES-MS 588 (m+1).

EXAMPLE 14

(S)-[1-{(4-Benzyloxy-benzyl)-[(2-hydroxy-2-phenyl-ethylcarbamoyl)-methyl]-carbamoyl}-2-(3H-imidazole-4-yl)-ethyl]-carbamic Acid Benzyl Ester The title compound can be prepared according to Example 15, Step 5, by substituting 2-amino-1-phenylethanol for β,β-dimethylphenethylamine hydrochloride. The title compound is obtained as a white foam (47%); ES-MS 662 (m+1).

EXAMPLE 15

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic Acid Benzyl Ester Step 1: (4-Benzyloxybenzylamino) Acetic Acid Methyl Ester To a mixture of glycine methyl ester hydrochloride (2.07 g, 16.5 mmol), and 4-benzyloxy-benzaldehyde (3.18 g, 15 mmol) in $CH_2Cl_2$ (50 mL) at 0° C. was added sodium triacetoxyborohydride (3.81 g, 18 mmol). The mixture was allowed to warm to room temperature and stirred overnight. Aqueous $NaHCO_3$ was added, and the mixture was stirred for 30 minutes. The aqueous layer was extracted 3 times with $CH_2Cl_2$. The combined organic extracts were washed with brine, dried over $MgSO_4$, and concentrated. Flash chromatography (ethyl acetate) gave 1.98 g (46%) of the title compound as a white solid; mp 57–58° C.

Step 2: N-[N-[(Phenylmethoxy)carbonyl]-L-histidyl-trityl]-N-[[4-(phenylmethoxy)phenyl]methyl]-alycine Methyl Ester To a suspension of Cbz-histidine-(trityl) (2.24 g, 4.21 mmol) in methylene chloride (25 mL) was added PyBOP (2.63 g, 5.05 mmol) and DIEA (1.46 mL; 8.4 mmol). The amine from Step 1 above (1.20 g, 4.21 mmol) was then added, and the mixture was stirred at room temperature overnight. The reaction mixture was concentrated in vacuo, the residue taken up in ethyl acetate, which was washed 3 times with saturated NaHCO$_3$, brine, dried over MgSO$_4$, and concentrated. Flash chromatography gave 1.68 g (72%) of the title compound as a white foam; ES-MS 557 (m+1).

Step 3: N-[N-[(Phenylmethoxy)carbonyl]-L-histidyl-trityl]-N-[[4-(henylmethoxy)phenyl]-methyl]-glycine To a solution of the ester from Step 2 (1.53 g, 2.75 rnmol) in THF (15 mL) and H$_2$O (5 mL) at 0° C. was added LiOH hydrate (0.14 g, 3.30 inmol), and the solution was stirred 5 hours at 0° C. The solution was concentrated, the residue taken up in H$_2$O, and the pH was adjusted to 4–5 with 1N HCl. The resulting mixture was concentrated and dried in vacuo to afford 1.65 g of the title compound as a white solid; FAB-MS 543 (m+1).

Step 4: β,β-Dimethylphenethylamine Hydrochloride

Sodium hydride (60% in oil) (17 g, 0.43 mol) was suspended in THF (150 mL) and cooled to 0° C. under nitrogen. Benzyl cyanide (22.2 g, 0.19 mol) in THF (30 mL) was added dropwise, and the reaction was left to stir for 1 hour. Iodomethane (24.9 mL, 0.4 mol) in THF (20 mL) was added dropwise at 0° C. The reaction was stirred at room temperature overnight, under nitrogen. The solution was filtered and the filtrate removed in vacuo. The residue was taken up in ethyl acetate (100 mL) and washed 3 times with 10% NaHSO$_3$, saturated NaHCO$_3$, brine, and dried over MgSO$_4$, concentrated; 22.74 g (92%).

Reduction of the above product was carried out in the presence of Raney nickel, in methanol/NH$_3$ The catalyst was removed and washed with methanol. The filtrate was concentrated, and diethyl ether (100 mL) was added to the residue. Concentrated HCl was added dropwise to precipitate the desired product; 24.8 g (86%).

Step 5: [1-{(4-Benzyloxy-benzyl)-[(2-methyl-2-phenyl-propylcarbamoyl)-methyl]-carbamoyl}-2-(3-trityl-3H-imidazole-4-yl)-ethyl]-carbamic Acid Benzyl Ester To a solution of the acid from Step 3 (2.9 g, 5.33 mmol) in methylene chloride was added HOBt hydrate (0.98 g, 6.39 mmol) and DCC (1.32 g, 6.39 mmol) followed by β,β-dimethylphenethylamine hydrochloride (from Step 4) (0.99 g, 5.33 mmol). Triethylamine (0.82 mL, 5.86 mmol) was added, and the mixture was stirred overnight at room temperature. The mixture was filtered, and the filtrate was diluted with CHCl$_3$, washed twice with saturated NaHCO$_3$, brine, dried over MgSO$_4$, and concentrated. Flash chromatography (2%–5% methanol/CHCl$_3$) gave 2.25 g (63%) of the title compound; ES-MS 917 (m+1).

Step 6: (S)-[1-{(4-benzyloxy-benzyl)-[(2-methyl-2-phenyl-propylcarbamoyl)-methyl]-carbamoyl}-2-(3H-imidazole-4-yl)-ethyl]-carbamic acid benzyl ester To a solution of the trityl compound from Step 5 (2.25 g, 2.4 mmol) was added glacial acetic acid (20 mL) and water (5 mL). The mixture was stirred at 90° C. for 30 minutes, then cooled and concentrated. The residue was taken up in ethyl acetate. The organic solution was washed twice with saturated NaHCO$_3$, brine, and dried over MgSO$_4$. The solution was concentrated and the compound purified by flash chromatography (0%–8% methanol in methylene chloride) to give the title compound (1.5 g, 2.2 mmol, 93%) as a white foam; ES-MS 674 (m+1).

EXAMPLE 16

(S)-[1-{(4-Benzyloxy-benzyl)-[(2-phenyl-butylcarbamoyl)-methyl]-carbamoyl}-2-(1H-imidazole-4-yl)-ethyl]-carbamic Acid Benzyl Ester The title compound can be prepared according to Example 15, Step 5, by substituting 5-ethylbenzeneethamine hydrochloride (Step 1) for β,β-dimethylphenethylamine hydrochloride. The title compound is obtained as a white foam (55%); ES-MS 674 (m+1).

Step 1: β-Ethylbenzeneethamine Hydrochloride

This compound is synthesized by catalytic reduction of 2-phenylbutyronitrile as exemplified in B. K. Trivedi, et al., *J. Med. Chem.*, 1993;36:3300–3307.

EXAMPLE 17

(S)-N-(4-Benzyloxy-benzyl)-3-(1H-imidazole-4-yl)-2-(3-phenyl-proponylamino)-N-[(2-phenyl-propylcarbamoyl)-methyl]-propionamide The title compound can be prepared according to Example 15, Step 2, by substituting phenylpropionyl-histidine-(trityl) (Steps 1 and 2) for Cbz-histidine-(trityl) and Step 5 by substituting β-methyl-phenethylamine for β,β-dimethylphenethylamine hydrochloride. The title compound is obtained as a white foam (45%); ES-MS 658 (m+1).

Step 1: Phenylpropionyl-histidine-(trityl) Methyl Ester

To a solution of histidine-(trityl) methyl ester hydrochloride (2.0 g, 4.2 mmol) and methyl piperidine (1.07 mL, 8.8 mmol) in methylene chloride at 0° C. was added slowly 3-phenylpropionyl chloride (0.62 mL, 4.2 mmol), and the solution was stirred overnight at room temperature. Ethyl acetate was added and washed twice with water, saturated NaHCO$_3$, brine, dried over MgSO$_4$, and concentrated. The product was obtained as a white foam; 2.0 g (88%).

Step 2: Phenylpropionyl-histidine-(trityl)

To a solution of the ester from Step 1 (2.0 g, 3.7 mmol) in THF:methanol (10 mL each) and water (2 mL) was added sodium hydroxide (0.44 g, 11 mmol), and the solution was stirred overnight at room temperature. The solvent was removed in vacuo and 5 mL of H$_2$O was added, followed by 1N HCl, to obtain pH 3. The product was extracted with ethyl acetate. The organic was washed with 1N HCl, brine, dried over MgSO$_4$, and concentrated. The product was obtained as a white foam (2.18 g); ES-MS 529 (m+1).

EXAMPLE 18

(S)-[1-{(4-Fluoro-benzyl)-[(2-phenyl-propylcarbamoyl)-methyl]-carbamoyl}-2-(1H-imidazole-4-yl)-ethyl]-carbamic Acid Benzyl Ester The title compound can be prepared according to Example 8, Step 4, by substituting β-methyl-phenethylamine for 2-pyridineethaneamine.HCl and in Step 1, by substituting p-fluoro-benzaldehyde for 4-benzyloxy-benzaldehyde. The title compound is obtained as a white foam (78%); ES-MS 572 (m+1).

EXAMPLE 19

(S)-(2-(1H-Imidazole-4-yl)-1-{(4-methyl-benzyl)-[(2-phenyl-propylcarbamoyl)-methyl]-carbamoyl}-ethyl)-carbamic Acid Benzyl Ester The title compound can be prepared according to Example 8, Step 4, by substituting β-methyl-phenethylamine for 2-pyridineethaneamine.HCl and in Step 1, by substituting p-methyl-benzaldehyde for 4-benzyloxy-benzaldehyde. The title compound is obtained as a white foam (66%); ES-MS 568 (m+1).

EXAMPLE 20

(S)-(2-(1H-Imidazole-4-yl)-1-{(4-methoxy-benzyl)-[(2-phenyl-propylcarbamoyl)-methyl]-carbamoyl}-ethyl)-carbamic Acid Benzyl Ester The title compound can be prepared according to Example 8, Step 4, by substituting β-methylphenethylamine for 2-pyridineethaneamine.HCl and in Step 1, by substituting p-methoxy-benzaldehyde for 4-benzyloxy-benzaldehyde. The title compound is obtained as a white foam (33%); ES-MS 583 (m+1).

EXAMPLE 21

(S)-[1-[}[2-(2-Amino-phenyl)-propylcarbamoyl]-methyl}-(4-benzyloxy-benzyl)-carbamoyl]-2-(3H-imidazole-4-yl)-ethyl]-carbamic Acid Benzyl Ester The title compound can be prepared according to Example 8, Step 4, by substituting 2-amino-5-methylphenethylamine (Step 1) for 2-pyridineethaneamine.HCl. The title compound is obtained as a- white foam (33%); ES-MS 675 (m+1).
Step 1: 2-Amino-β-methylphenethylamine
Reduction of 4-methyl-cinnoline (10 g, 69.5 mmol) in methanol (100 mL), using Raney nickel (3 g). The catalyst was removed and washed with methanol. The filtrate was treated with an excess of HCl in isopropanol; ether was then added and the solution cooled. The precipitate was filtered and dried; 9.4 g (60%).

EXAMPLE 22

(S)-[1-{(4-Fluoro-benzyl)-[(2-methyl-2-phenyl-propylcarbamoyl)-methyl]-carbamoyl}-2-(1H-imidazole-4-yl)-ethyl]-carbamic Acid Benzyl Ester The title compound can be prepared according to Example 15, Step 1, by substituting p-fluoro-benzaldehyde for 4-benzyloxy benzaldehyde. The title compound is obtained as a white foam (87%); ES-MS 586 (m+1).

EXAMPLE 23

(S)-[1-{Benzyl-[(2-phenyl-propylcarbamoyl)-methyl]-carbamoyl}-2-(1H-imidazole-4-yl)-ethyl]-carbamic Acid Benzyl Ester The title compound can be prepared according to Example 8, Step 4, by substituting β-methyl-phenethylamine for 2-pyridineethaneamine.HCl and in Step 1, by substituting benzaldehyde for 4-benzyloxy-benzaldehyde. The title compound is obtained as a white foam (57%); ES-MS 554 (m+1).

EXAMPLE 24

(S)-[1-((4-Benzyloxy-benzyl)-{[2-(2-chloro-phenyl)-2-phenyl-ethylcarbamoyl]-methyl}-carbamoyl)-2-(1H-imidazole-4-yl)-ethyl]-carbamic Acid Benzyl Ester The title compound can be prepared according to Example 8, Step 4, by substituting o-chloro-β-phenyl-phenethylamine hydrochloride (Steps 1 and 2) for 2-pyridineethaneamine.HCl. The title compound is obtained as a white foam (37%); ES-MS 756 (m+1).
Step 1: 2-Phenyl-3-(2-chloro-phenyl) Cyanide
Bromine (2 mL) was added dropwise to 2-chloro-benzylcyanide (5 g, 32 mmol) at 90° C. over 1 hour with stirring. Nitrogen was passed over the reaction to remove HBr. The reaction was heated for 15 minutes, and benzene (2 mL) was then added. This solution was added dropwise to a refluxing solution of $AlC_3$ (4.2 g, 32 mmol) in benzene (15 mL) over 2 hours. The reaction was refluxed 1 hour. The reaction was cooled and poured onto ice (200 g) and concentrated HCl (20 mL). The aqueous layer was extracted with diethyl ether and diethyl ether:benzene (1:1). The organic solution was washed twice with $H_2O$, saturated $NaHCO_3$, brine, and dried over $Na_2SO_4$, and concentrated to give an orange oil; 6.3 g (86%).
Step 2: o-Chloro-β-phenyl-phenethylamine Hydrochloride
Reduction of the product from Step 1 was carried out in the presence of Raney nickel, in methanol/$NH_3$. The catalyst was removed and washed with methanol. The filtrate was concentrated and ethanol (100 mL) was added to the residue. Concentrated HCl was added slowly until pH 3. The volume of ethanol was reduced in vacuo to about 5 mL, and the HCl salt was precipitated by the addition of diethyl ether; 1.84 g (68%).

EXAMPLE 25

(S)-[1-{(4-Benzyloxy-benzyl)-[(2-ethyl-2-phenyl-butylcarbamoyl)-methyl]-carbamoyl}-2-(3H-imidazole-4-yl)-ethyl]-carbamic Acid Benzyl Ester The title compound can be prepared according to Example 15, Step 5, by substituting β,β-diethylbenzeneethaneamine hydrochloride (Step 1) for β,β-dimethylphenethylamine hydrochloride. The title compound is obtained as a white foam (52%); ES-MS 702 (m+1).
Step 1: β,β-Diethylbenzeneethaneamine Hydrochloride
This compound is synthesized by diethylating phenylacetonitrile followed by catalytic reduction as exemplified in B. K. Trivedi, et al., *J. Med. Chem.*, 1993;36:3300–3307.

EXAMPLE 26

(S)-N-(4-Benzyloxy-benzyl)-2-(3-benzyl-ureido)-3-(1H-imidazole-4-yl)-N-[(2-phenyl-propylcarbamoyl)-methyl]-propionamide The title compound can be prepared according to Example 15, Step 2, by substituting benzyl-urea-histidine-(trityl) (Steps 1 and 2, Example 6) for Cbz-histidine-(trityl), and Step 5, by substituting β-methyl-phenethylamine hydrochloride for β,β-dimethylphenethylamine hydrochloride. The title compound is obtained as a white foam (64%); ES-MS 659 (m+1).

EXAMPLE 27

(S)-N-(4-Benzyloxy-benzyl)-2-(3-benzyl-ureido)-3-(1H-imidazole-4-yl)-N-[(2-phenyl-butylcarbamoyl)-methyl]-propionamide The title compound can be prepared according to Example 15, Step 2, by substituting benzyl-urea-histidine-(trityl)-HCl (Steps 1 and 2, Example 6) for Cbz-histidine-(trityl), and Step 5, by substituting β-ethylbenzeneethamine hydrochloride (Step 1, Example 16) for β,β-dimethylphenethylamine hydrochloride. The title compound is obtained as a white foam (93%); ES-MS 673 (m+1).

EXAMPLE 28

(S)-[1-{(2-Chloro-benzyl)-[(2-phenyl-propylcarbamoyl)-methyl]-carbamoyl}-2-(1H-imidazole-4-yl)-ethyl]-carbamic Acid Benzyl Ester The title compound can be prepared according to Example 8, Step 4, by substituting β-methylphenethylamine for 2-pyridineethaneamine.HCl and in Step 1, by substituting o-chloro-benzaldehyde for 4-benzyloxy-benzaldehyde. The title compound is obtained as a white foam (40%); ES-MS 588 (m+1).

EXAMPLE 29

(S)-[1-{(4-Bromo-benzyl)-[(2-phenyl-propylcarbamoyl)-methyl]-carbamoyl}-2-(1H-imidazole-4-yl)-ethyl]-carbamic Acid Benzyl Ester The title compound can be prepared according to Example 8, Step 4, by substituting β-methylphenethylamine for 2-pyridineethaneamine-HCl and in Step 1, by substituting p-bromo-benzaldehyde for 4-benzyloxy-benzaldehyde. The title compound is obtained as a white foam (91%); ES-MS 633 (m+1).

EXAMPLE 30

(S)-[1-{(3-Chloro-benzyl)-[(2-phenyl-propylcarbamoyl)-methyl]-carbamoyl}-2-(1H-imidazole-4-yl)-ethyl]-carbamic Acid Benzyl Ester The title compound can be prepared according to Example 8, Step 4, by substituting β-methylphenethylamine for 2-pyridineethaneamine.HCl and in Step 1, by substituting m-chloro-benzaldehyde for 4-benzyloxy-benzaldehyde. The title compound is obtained as a white foam (10%); ES-MS 588 (m+1).

EXAMPLE 31

(S)-[1-{(4-Chloro-benzyl)-[(2-methyl-2-phenyl-propylcarbamoyl)-methyl]-carbamoyl}-2-(1H-imidazole-4-yl)-ethyl]-carbamic Acid Benzyl Ester The title compound can be prepared according to Example 15, Step 1, by substituting p-chloro-benzaldehyde for 4-benzyloxy-benzaldehyde. The title compound is obtained as a white foam (33%); ES-MS 602 (m+1).

EXAMPLE 32

(S)-[1-((4-Benzyloxy-benzyl)-{[2-(2-chloro-phenyl)-propylcarbamoyl]-methyl}-carbamoyl)-2-(1H-imidazole-4-yl)-ethyl]-carbamic Acid Benzyl Ester The title compound can be prepared according to Example 8, Step 4, by substituting o-chloro-β-methyl-phenethylamine hydrochloride (Steps 1 and 2) for 2-pyridineethaneamine.HCl. The title compound is obtained as a white foam (41%); ES-MS 694 (m+1).

Step 1: 2-Methyl-3-(2-chloro-phenyl) Cyanide

To a suspension of $NaNH_2$ powder (0.6 g, 15.5 mmol) in THF (15 mL), 2-chlorophenylacetonitrile (2 g, 13 mmol) in THF (10 mL) was added. The mixture was refluxed for 2 hours. A solution of methyl iodide (2.18 g, 15.5 mnmol) in THF (10 mL) was then added, and the solution was refluxed for an additional 3 hours. The reaction was cooled and treated with $H_2O$. The organic layer was separated and washed twice with 5% $Na_2S_2O_3$, brine, dried over $Na_2SO_4$, and concentrated; 1.93 g (93%).

Step 2: o-Chloro-β-methyl Phenethylamine Hydrochloride

Reduction of the product from Step 1 was carried out in the presence of Raney nickel, in methanol/$NH_3$. The catalyst was removed and washed with methanol. The filtrate was concentrated and diethyl ether (100 mL) was added to the residue. Concentrated HCl was added dropwise to precipitate the compound; 1.06 g (44%).

EXAMPLE 33

(S)-(2-(1H-Imidazole-4-yl)-1-{(2-methoxy-benzyl)-[(2-phenyl-propylcarbamoyl)-methyl]-carbamoyl}-ethyl)-carbamic Acid Benzyl Ester The title compound can be prepared according to Example 8, Step 4, by substituting β-methylphenethylamine for 2-pyridineethaneamine.HCl and in Step 1, by substituting o-methoxy-benzaldehyde for 4-benzyloxy-benzaldehyde. The title compound is obtained as a white foam (15%); ES-MS 584 (m+1).

EXAMPLE 34

(S)-(2-(1H-Imidazole-4-yl)-1-{[(2-phenyl-propylcarbamoyl)-methyl]-[4-(pyridin-4-ylmethoxy)-benzyl]-carbamoyl}-ethyl)-carbamic Acid Benzyl Aster The title compound can be prepared according to Example 15, Step 1, by substituting 4-[(4-pyridyl)-methyloxy]-benzaldehyde (Step 1) for 4-benzyloxy-benzaldehyde and Step 5 by substituting β-methylphenethylamine for β,β-dimethylphenethylamine hydrochloride. The title compound is obtained as a white foam (67%); ES-MS 661 (m+1).

Step 1: 4-f(4-Pyridyl)-methyloxyl-benzaldehyde

This compound is synthesized as exemplified in *J. Het. Chem.*, 1988;25:129.

EXAMPLE 35

(S)-(2-(1H-Imidazole-4-yl)-1-{(3-methoxy-benzyl)-[(2-phenyl-propylcarbamoyl)-methyl]-carbamoyl}-ethyl)-carbamic Acid Benzyl Ester The title compound can be prepared according to Example 8, Step 4, by substituting β-methylphenethylamine for 2-pyridineethaneamine.HCl and in Step 1, by substituting m-methoxy-benzaldehyde for 4-benzyloxy-benzaldehyde. The title compound is obtained as a white foam (14%); ES-MS 584 (m+1).

EXAMPLE 36

(S)-(2-(1H-Imidazole-4-yl)-1-{[(2-phenyl-propylcarbamoyl)-methyl]-[4-(pyridin-3-ylmethoxy)-benzyl]-carbamoyl}-ethyl)-carbamic Acid Benzyl Ester The title compound can be prepared according to Example 15, Step 1, by substituting 4-[(3-pyridyl)-methyloxy]-benzaldehyde (Step 1) for 4-benzyloxy-benzaldehyde and Step 5 by substituting β-methylphenethylamine for β,β-dimethylphenethylamine hydrochloride. The title compound is obtained as a white foam (59%); ES-MS 661 (m+1).

Step 1: 4-[(3-Pyridyl)-methyloxy] Benzaldehyde

This compound is synthesized as exemplified in *J. Het. Chem.*, 1988;25:129.

EXAMPLE 37

(S)-(2-(1H-Imidazole-4-yl)-1-{naththalen-1-ylmethyl-[(2-phenyl-propylcarbamoyl)-methyl]-carbamoyl}-ethyl)-carbamic Acid Benzyl Ester The title compound can be prepared according to Example 15, Step 1, by substituting 1-naphthalene-carboxaldehyde for 4-benzyloxy-benzaldehyde and Step 5 by substituting β-methylphenethylamine for β,β-dimethylphenethylamine hydrochloride. The title compound is obtained as a white foam (15%); ES-MS 604 (m+1).

EXAMPLE 38

(S)-{2-(1H-Imidazole-4-yl)-1-[[(2-phenyl-propylcarbamoyl)-methyl]-(4-trifluoromethyl-benzyl)-carbamoyl]-ethyl}-carbamic Acid Benzyl Ester The title compound can be prepared according to Example 8, Step 4, by substituting β-methylphenethylamine for 2-pyridineethaneamine.HCl and in Step 1, by substituting p-trifluoromethyl-benzaldehyde for 4-benzyloxy-benzaldehyde. The title compound is obtained as a white foam (13%); ES-MS 622 (m+1).

EXAMPLE 39

(S)-(2-(1H-Imidazole-4-yl)-1-{[(2-methyl-2-phenyl-propylcarbamoyl)-methyl]-pyridin-3-ylmethyl-carbamoyl}-ethyl)-carbamic Acid Benzyl Ester The title compound can be prepared according to Example 15, Step 1 by substituting 3-pyridin-aldehyde for 4-benzyloxy-benzaldehyde. The title compound is obtained as a white foam (84%); ES-MS 569 (m+1).

EXAMPLE 40

(S)-(2-(1H-Imidazole-4-yl)-1-{[(2-methyl-2-phenyl-propylcarbamoyl)-methyl]-[4-(pyridin-2-ylmethoxy)-benzyl]-carbamoyl}-ethyl)-carbamic Acid Benzyl Ester The title compound can be prepared according to Example 15, Step 1, by substituting 4-[(2-pyridyl)-methyloxy]-benzaldehyde (Step 1) for 4-benzyloxy-benzaldehyde. The title compound is obtained as a white foam (62%); ES-MS 675 (m+1).
Step 1: 4-[(2-Pyridyl)-methyloxy]-benzaldehyde
This compound is synthesized as exemplified in J. Het. Chem., 1988;25:129.

EXAMPLE 41

(S)-2-(3-Benzyl-3-methyl-ureido)-N-(4-benzyloxy-benzyl)-3-(1H-imidazole-4-yl)-N-[(2-methyl-2-phenyl-propylcarbamoyl)-methyl]-propionamide The title compound can be prepared according to Example 15, Step 2, by substituting N-methyl-N-benzyl-urea-histidine-(trityl) (Steps 1 and 2) for Cbz-histidine-(trityl). The title compound is obtained as a white foam (79%); ES-MS 687 (m+1).
Step 1: N-methyl-N-benzyl-urea-histidine-(trityl) Methyl Ester Histidine-(trityl) methyl ester hydrochloride (2.0 g, 4.2 mmol) was suspended in methylene chloride (20 mL,) and the solution was washed twice with saturated $NaHCO_3$, and brine, dried over $MgSO_4$, and cooled to 0° C. Triethylamine (0.65 mL, 8.8 mmol) and 4-nitrophenyl chloroformate (0.93 g, 4.7 mmol) was added. The reaction was stirred at 0° C. under nitrogen for 1.5 hours. N-benzyl-N-methylamine (1.14 mL, 8.8 mmol) in methylene chloride (10 mL) was then added slowly, and the reaction was stirred at room temperature overnight, under nitrogen. The solvent was removed, and ethyl acetate was added to the residue. The organic solution was washed twice with $H_2O$, saturated $NaHCO_3$, brine, and dried over $MgSO_4$, and concentrated. Chromatography using 1:1 ethyl acetate: hexanes gave a foam; 1.19 g (50%).
Step 2: N-methyl-N-benzyl-urea-histidine-(trityl) The methyl ester from Step 1 (1.19 g, 2.1 mmol) was dissolved in THF:methanol (10 mL of each). 1N NaOH (6.3 mL, 6.3 mmol) was added, and the reaction was stirred overnight. The solvent was removed. 1N HCl (6.3 mL) was added and extracted with ethyl acetate. The organic solution was then washed twice with brine, dried over $MgSO_4$, and concentrated to give a white foam; 1.4 g.

EXAMPLE 42

(S)-[1-{Benzyl-[(2-methyl-2-phenyl-propylcarbamoyl)-methyl]-carbamoyl}-2-(1H-imidazole-4-yl)-ethyl]-carbamic Acid Benzyl Ester The title compound can be prepared according to Example 8, Step 4, by substituting β,β-dimethylphenethylamine hydrochloride for 2-pyridineethaneamine.HCl and in Step 1, by substituting benzaldehyde for 4-benzyloxy-benzaldehyde. The title compound is obtained as a white foam (42%); ES-MS 568 (m+1).

EXAMPLE 43

(S)-(2-(1H-Imidazole-4-yl)-1-}(2-methyl-benzyl)-[(2-phenyl-propylcarbamoyl)-methyl]-carbamoyl}-ethyl)-carbamic Acid Benzyl Ester The title compound can be prepared according to Example 8, Step 4, by substituting β-methylphenethylamine for 2-pyridineethaneamine.HCl and in Step 1, by substituting o-methyl-benzaldehyde for 4-benzyloxy-benzaldehyde. The title compound is obtained as a white foam (49%); ES-MS 568 (m+1).

EXAMPLE 44

(S)-(2-(1H-Imidazole-4-yl)-1-{(4-methoxy-benzyl)-[(2-methyl-2-phenyl-propylcarbamoyl)-methyl]-carbamoyl}-ethyl)-carbamic Acid Benzyl Ester The title compound can be prepared according to Example 8, Step 4, by substituting β,β-dimethylphenethylamine hydrochloride for 2-pyridineethaneamine.HCl and in Step 1, by substituting p-methoxy-benzaldehyde for 4-benzyloxy-benzaldehyde. The title compound is obtained as a white foam (16%); ES-MS 598 (m+1).

EXAMPLE 45

(S)-[1-}(4-Benzyloxy-benzyl)-[(2-cyano-2-phenyl-ethylcarbamoyl)-methyl]-carbamoyl}-2-(1H-imidazole-4-yl)-ethyl]-carbamic Acid Benzyl Ester The title compound can be prepared according to Example 15, Step 5, by substituting β-cyano-phenethylamine hydrochloride (Step 1) for β,β-dimethylphenethylamine hydrochloride. The title compound is obtained as a white foam (47%); ES-MS 671 (m+1).
Step 1: β-Cyano-phenethylamine Hydrochloride
This compound is synthesized according to the U.S. Pat. No. 4,760,089, 1988, which is hereby incorporated by reference.

EXAMPLE 46

(S)-(2-(1H-Imidazole-4-yl)-1-{[(2-methyl-2-phenyl-propylcarbamoyl)-methyl]-pyridin-2-ylmethyl-carbamoyl}-ethyl)-carbamic Acid Benzyl Ester The title compound can be prepared according to Example 15, where Step 1 is carried out as shown below. The title compound is obtained as a white foam (63%); ES-MS 569 (m+1).
Step 1: [(2-Pyridyl)-methylamino)]-acetic Acid Methyl Ester A solution of 2-aminomethylpyridine (5.0 g, 46.2 mmol) in acetonitrile (100 mL) was treated with methyl bromoacetate (4.3 mL, 46.2 mmol) and triethylamine (6.5 mL, 46.2 mmol). After stirring for 1 hour at room temperature, the solution was heated at reflux overnight. The solution was diluted with ethyl acetate and washed with saturated $NaHCO_3$, water, and brine, dried over $MgSO_4$, and concentrated. Chromatography eluting with 3% methanol in chloroform gave 2.73 g (33%) of pure product, as an oil.

EXAMPLE 47

(S)-(2-(1H-Imidazole-4-yl)-1-{(3-methyl-benzyl)-
[(2-phenyl-propylcarbamoyl)-methyl]-carbamoyl}-
ethyl)-carbamic Acid Benzyl Ester The title compound can be prepared according to Example 8, Step 4, by substituting β-methylphenethylamine for 2-pyridineethaneamine.HCl and in Step 1, by substituting m-methyl-benzaldehyde for 4-benzyloxy-benzaldehyde. The title compound is obtained as a white foam (52%); ES-MS 568 (m+1).

EXAMPLE 48

(S)-[1-{(4-Dimethylamino-benzyl)-[(2-phenyl-
propylcarbamoyl)-methyl]-carbamoyl}-2-(1H-
imidazole-4-yl)-ethyl]-carbamic Acid Benzyl Ester The title compound can be prepared according to Example 8, Step 4, by substituting β-methylphenethylamine for 2-pyridineethaneamine.HCl and in Step 1, by substituting p-dimethylamino-benzaldehyde for 4-benzyloxy-benzaldehyde. The title compound is obtained as a white foam (36%); ES-MS 597 (m+1).

EXAMPLE 49

(S)-(2-(1H-Imidazole-4-yl)-1-{[(2-methyl-2-phenyl-
propylcarbamoyl)-methyl]-[4-(pyridin-4-
ylmethoxy)-benzyl]-carbamoyl}-ethyl)-carbamic
Acid Benzyl Ester The title compound can be prepared according to Example 15, Step 1, by substituting 4-[(4-pyridyl)-methyloxy]-benzaldehyde (Step 1) for 4-benzyloxy-benzaldehyde. The title compound is obtained as a white foam (93%); ES-MS 675 (m+1).
Step 1: 4-[(4-Pyridyl)-methyloxy]-benzaldehyde
This compound is synthesized as exemplified in *J. Het. Chem.*, 1988;25:129.

EXAMPLE 50

(S)-(2-(1H-Imidazole-4-yl)-1-{[(2-methyl-2-phenyl-
propylcarbamoyl)-methyl]-[4-(pyridin-3-
ylmethoxy)-benzyl]-carbamoyl}-ethyl)-carbamic
Acid Benzyl Ester The title compound can be prepared according to Example 15, Step 1, by substituting 4-[(3-pyridyl)-methyloxy]-benzaldehyde (Step 1) for 4-benzyloxy-benzaldehyde. The title compound is obtained as a white foam (56%); ES-MS 675 (m+1).
Step 1: 4-[(3-Pyridyl)-methyloxy]-benzaldehyde
This compound is synthesized as exemplified in *J. Het. Chem.*, 1988;25:129.

EXAMPLE 51

(S)-[1-{Biphenyl-4-ylmethyl-[(2-phenyl-
propylcarbamoyl)-methyl]-carbamoyl}-2-(1H-
imidazole-4-yl)-ethyl]-carbamic Acid Benzyl Ester The title compound can be prepared according to Example 15, Step 1, by substituting p-phenyl-benzaldehyde for 4-benzyloxy-benzaldehyde and in Step 5, by substituting β-methyl-phenethylamine hydrochloride for β,β-dimethylphenethylamine hydrochloride. The title compound was obtained as a white foam (33%); ES-MS 630 (m+1).

EXAMPLE 52

(S)-[1-{Biphenyl-4-ylmethyl-[(2-methyl-2-phenyl-
propylcarbamoyl)-methyl]-carbamoyl}-2-(1H-
imidazole-4-yl)-ethyl]-carbamic Acid Benzyl Ester The title compound can be prepared according to Example 15, Step 1, by substituting p-phenyl-benzaldehyde for 4-benzyloxy-benzaldehyde. The title compound was obtained as a white foam (32%); ES-MS 644 (m+1).

EXAMPLE 53

(S)-[1-((4-Benzyloxy-benzyl)-}[2-(2-chloro-phenyl)-
ethylcarbamoyl]-methyl}-carbamoyl)-2-(1H-
imidazole-4-yl)-ethyl]-carbamic Acid Benzyl Ester The title compound can be prepared according to Example 7, Step 1, by substituting 2-chloro-phenethylamine for 2-[(2-fluorophenyl)-ethyl]-amine. The title compound is obtained as a white foam (89%); ES-MS 681 (m+1).

EXAMPLE 54

(S)-[1-{(4-Benzyloxy-benzyl)-[(2-methyl-2-henyl-
propylcarbamoyl)-methyl]-carbamoyl}-2-(1H-
imidazole-4-yl)-ethyl]-carbamic acid thiophen-3-
ylmethyl Ester The title compound can be prepared according to Example 15, Step 2, by substituting 3-thiophenemethyl-oxycarbonyl-histidine-(trityl) (Steps 1 and 2) for Cbz-histidine-(trityl). The title compound is obtained as a white foam (40%); ES-MS 680 (m+1).
Step 1: 3-Thiophenemethyloxycarbonyl-histidine-(trityl) Methyl Ester 3-Thiophene methanol (0.43 mL, 4.6 mmol), triethylamine (0.64 mL, 4.6 mmol), and 4-nitrophenyl chloroformate (0.92 g, 4.6 mmol) were dissolved in methylene chloride (20 mL) and cooled to 0° C. under nitrogen. After 1 hour, histidine-(trityl) methyl ester hydrochloride (2 g, 4.2 mmol) and triethylamine (1.28 mL, 9.2 nmol) in methylene chloride (10 mL) were added. The reaction was stirred overnight. The solvent was removed in vacuo. Ethyl acetate and water were added. The organic layer was washed with saturated NaHCO$_3$, brine, dried over MgSO$_4$, and concentrated to give a yellow oil. Flash chromatography (1:1 ethyl acetate:hexanes) yielded a white foam; 1.15 g (50%).
Step 2: 3-Thiophenemethyloxycarbonyl-histidine-(trityl)

To a solution of the ester from Step 1 (1.15 g, 2.1 mmol) in THF (10 mL) and methanol (10 mL) was added 1N NaOH (6.3 mL, 6.3 mmol) and the solution was stirred overnight at room temperature. The solution was concentrated, 1N HCl (6.3 mL) was added, and the product extracted with ethyl acetate, which was washed twice with brine, dried over MgSO$_4$ and concentrated to give a white foam; 1.12 g (99%).

EXAMPLE 55

(S)-[1-{(4-Chloro-benzyl)-[1-(2-methyl-2-phenyl-
propylcarbamoyl)-ethyl]-carbamoyl}-2-(3H-
imidazole-4-yl)-ethyl]-carbamic Acid Benzyl Ester The title compound can be prepared according to Example 15, Step 1, by substituting alanine methyl ester hydrochloride for glycine methyl ester hydrochloride and in Step 2 by substituting 1-hydroxy-7-azabenzotriazole (HOAt) and O-(7-azabenzotriazol-1-yl)-1,1,3,3-tetramethyluronium hexafluorophosphate (HATU) for PyBOB. The title compound is obtained as a white foam (78%); ES-MS 617 (m+1).

EXAMPLE 56

(S)-(2-(1H-Imidazole-4-yl)-1-{(4-methyl-benzyl)-[(2-methyl-2-phenyl-propylcarbamoyl)-methyl]-carbamoyl}- ethyl)-carbamic Acid Benzyl Ester The title compound can be prepared according to Example 15, Step 1, by substituting 4-methyl-benzaldehyde for 4-benzyloxy-benzaldehyde. The title compound is obtained as a white foam (74%); ES-MS 582 (m+1).

EXAMPLE 57

(S)-(2-(1H-Imidazole-4-yl)-1-{(2-methoxy-benzyl)-[(2-methyl-2-phenyl-propylcarbamoyl)-methyl]-carbamoyl}-ethyl)-carbamic Acid Benzyl Ester The title compound can be prepared according to Example 8, Step 1, by substituting 2-methoxy-benzaldehyde for 4-benzyloxy-benzaldehyde and in Step 4, by substituting β,β-dimethylphenethylamine (Example 15, Step 4) for 2-pyridine-ethaneamine hydrochloride. The title compound is obtained as a white foam (11%); ES-MS 598 (m+1).

EXAMPLE 58

(S)-2-(3-Benzyl-3-methyl-ureido)-N-(4-chloro-benzyl)-3-(1H-imidazole-4-yl)-N-[(2-methyl-2-phenyl-propylcarbamoyl)-methyl]-propionamide The title compound can be prepared according to Example 15, Step 1, by substituting 4-chloro-benzaldehyde for 4-benzyloxy-benzaldehyde and in Step 2, by substituting N-methyl-N-benzyl-urea-histidine-(trityl) (Example 41, Steps 1 and 2) for Cbz-histidine-(trityl). The title compound is obtained as a white foam (72%); ES-MS 616 (m+1).

EXAMPLE 59

(S)-(2-(1H-Imidazole-4-yl)-1-{(3-methoxy-benzyl)-[(2-methyl-2-phenyl-propylcarbamoyl)-methyl]-carbamoyl}-ethyl)-carbamic Acid Benzyl Ester The title compound can be prepared according to Example 8, Step 1, by substituting 3-methoxy-benzaldehyde for 4-benzyloxy-benzaldehyde and in Step 4, by substituting β,β-dimethylphenethylamine (Example 15, Step 4) for 2-pyridine-ethaneamine hydrochloride. The title compound is obtained as a white foam (5%); ES-MS 598 (m+1).

EXAMPLE 60

(S)-(2-(1H-Imidazole-4-yl)-1-{[(2-methyl-2-phenyl-propylcarbamoyl)-methyl]-[2-(pyridin-4-ylmethoxy)-benzyl]-carbamoyl}-ethyl)-carbamic Acid Benzyl Ester The title compound can be prepared according to Example 15, Step 1, by substituting 2-[(4-pyridyl)-methyloxy]-benzaldehyde (Step 1) for 4-benzyloxy-benzaldehyde. The title compound is obtained as a white foam (61%); ES-MS 676 (m+1).
Step 1: 2-[(4-Pyridyl)-methyloxy]-benzaldehyde A solution of salicylaldehyde (5 g, 40.9 mmol) in DMSO (75 mL) was treated with crushed potassium hydroxide (5.4 g, 81.8 mmol) and allowed to stir at room temperature for 1 hour. This was then treated with 4-picolyl chloride hydrochloride (6.8 g, 40.9 mmol) and the dark mixture allowed to stir overnight. The mixture was poured into water and extracted twice with ethyl acetate. The combined ethyl acetate extracts were washed with 5% NaOH, three times with water then with brine. Drying over $MgSO_4$ and removal of the solvent under reduced pressure gave the crude product. This was taken up in ethyl acetate, treated with charcoal, filtered, and the solvent removed under reduced pressure to give 5.42 g (62.1%) of the product as an oil; MS-CI 214 (M+1).

EXAMPLE 61

[1-{Cyclohexylmethyl-[(2-phenyl-propylcarbamoyl)-methyl]-carbamoyl}-2-(3H-imidazole-4-yl)-ethyl]-carbamic Acid Benzyl Ester The title compound can be prepared according to Example 8, Step 1, by substituting cyclohexane-carboxaldehyde for 4-benzyloxy-benzaldehyde and in Step 4, by substituting 5-methyl-phenethyl-amine for 2-pyridineethaneamine HCl. The title compound is obtained as a white foam (16%); MS-ES 559 (M+H).

EXAMPLE 62

(S)-(2-(1H-Imidazol-4-yl)-1-{isobutyl-[(2-phenyl-propylcarbamoyl)-methyl]-carbamoyl}-ethyl)-carbamic Acid Benzyl Ester Step 1: $N^\alpha$-Boc-N-[(2-phenyl-propylcarbamoyl)-methyl]-glycinamide To a solution of Boc-glycine (2.1 g, 12 mmol) in methylene chloride (100 mL) was added β-methyl-phenethylamine (1.91 mL, 13.2 mmol), 1-hydroxybenzo-triazole (Hobt) (1.78 g, 13.2 nmol), dicyclohexyl-carbodiimide (DCC) (0.5 M DCC in methylene chloride; 26 mL, 13.2 mmol) and diisopropylethylamine (4.17 mL, 24 mmol). The reaction was stirred at room temperature overnight. The reaction solution was filtered. The filtrate was washed 3 times with brine. The organic solution was dried over $MgSO_4$ and concentrated. Flash chromatography (5% methanol in chloroform) gave 3.5 g (100%) of the title compound as a white solid; CI-MS 293 (m+1).
A Step 2: N-[2-phenyl-propylcarbamoyl)-methyl]-glycinamide trifluoroacetic acid salt To a solution of the compound from Step 1 above (3.5 g, 12 mmol) in methylene chloride (35 mL) was added trifluoroacetic acid (15 mL). The solution was stirred for 2 hours, then concentrated. The residue was dissolved in methylene chloride and reconcentrated to give the title compound as an oil. This was used in the next reaction without characterization.
Step 3: N-[(2-phenyl-DroTylcarbamoyl)-methyl]-Nα-(4-benzyloxy-benzyl)-glycinamide hydrochloride salt To a suspension of the compound from Step 2 above (1.16 g, 6 mmol), isobutyraldehyde (0.274 mL, 3 mmol), and sodium acetate (0.59 g, 7.25 mmol) in methylene chloride (25 mL) were added. The solution was cooled to 0° C., and sodium triacetoxyborohydride (1.92 g, 9.1 mmol) was added. The reaction was allowed to warm to room temperature and was stirred overnight. The reaction was treated with a saturated aqueous $NaHCO_3$ solution, and the layers were separated. The aqueous layer was extracted with methylene chloride (2×20 mL). The organic layers were combined and washed 3 times with brine, dried over $MgSO_4$, and concentrated.

The product was purified by flash chromatography (5% methanol in chloroform) to give 0.22 g (15%) of the title compound: CI-MS 249 (m+1).

Step 4: (2-(1-trityl-1H-imidazole-4-yl)-1-{isobutyl-[(2-phenyl-propylcarbamoyl)-methyl]-carbamoyl}-ethyl)-carbamic Acid Benzyl Ester To a solution of (S)-(2-benzyloxycarbonylamino-3-(1-trityl)-1H-imidazole-4-yl)-propionic acid (Cbz-histidine-(trityl)) (Hudsspeth J. P.; Kaltenbronn J. S.; Repine J. T.; Roark W. H.; Stier M. A. Renin Inhibitors III. U.S. Pat. No. 4,735,933; 1988), (0.532 g, 1.0 mmol) in methylene chloride (50 mL) was added O-(7-azabenzotriazol-1-yl)-N,N,N',N'-tetramethyluronium hexafluorophosphate (HATU) (0.67 g, 1.7 mmol), 1-hydroxy-7-azabenzotriazole (HOAt) (0.24 g, 1.7 mmol) and diisopropylethylamine (1.08 mL, 6.2 mmol). The mixture was then treated with amine (0.22 g, 0.88 mmol) from Step 3 above, and stirred overnight. The reaction solution was concentrated and the residue dissolved in ethyl acetate (25 mL). The organic solution was washed 3 times with 5% citric acid, 5% $NaHCO_3$ and brine, dried over $MgSO_4$, and concentrate. The product was used without further purification in the next step.

Step 5: (S)-(2-(1H-imidazole-4-yl)-1-{isobutyl-[(2-phenyl-propylcarbamoly)-methyl]-carbamoyl}-ethyl)-carbamic Acid Benzyl Ester To a solution of the trityl compound (0.64 g, 0.86 mmol) from Step 4 above in methylene chloride (25 mL) was added TFA (25 mL). The solution was stirred for 3 hours, then concentrated. The residue was partitioned between a saturated aqueous solution of $NaHCO_3$ and ethyl acetate. The layers were separated and the aqueous layer was extracted with ethyl acetate (2×20 mL). The organic layers were combined, dried over $MgSO_4$, and concentrated. Purification by reversed-phase high pressure liquid chromatography (eluents: 0.1% TFA in water and 01% TFA in acetonitrile) was carried out and gave 0.060 g (13%) of the title compound: ES-MS 520 (m+1).

PFT Inhibitory Activity

The protein:farnesyl transferase (PFT) or farnesyl protein transferase (FPT) inhibitory activity of compounds of the present invention were assayed in HEPES buffer (pH 7.4) containing 5 mM potassium phosphate and 20 $\mu$M $ZnCl_2$. The solution also contained 5 mM DTT (dithiothreitol), 5 mM $MgCl_2$, and 0.1% PEG 8000. Assays were performed in 96 well plates (Wallec) and employed solutions composed of varying concentrations of a compound of the present invention in 100% DMSO (dimethylsulfoxide). Upon addition of both substrates, radiolabeled farnesyl pyrophosphate ([$1^3$H], specific activity 15–30 Ci/mmol, final concentration 134 nM) and (biotinyl)-Ahe-Thr-Lys-Cys-Val-Ile-Met ([3aS[3a alpha, 4 beta, 6a alpha]-hexahydro-2-oxo-1H-thieno[3,4-d] imidazole-5-pentanoic acid]-[7-aminoheptanoic acid]-Thr-Lys-Cys-Val-Ile-Met) (Ahe is 7-aminoheptanoic acid, Thr is threonine, Lys is lysine, Cys is cysteine, Val is valine, Ile is isoleucine and Met is methionine) (final concentration 0.2 $\mu$M), the enzyme reaction was started by addition of SF9 affinity purified rat farnesyl protein transferase. After incubation at 30° C. for 30 minutes, the reaction was terminated by diluting the reaction 2.5-fold with a stop buffer containing 1.5 M magnesium acetate, 0.2 M $H_3PO_4$, 0.5% BSA (bovine serum albumin), and strepavidin beads (Amersham) at a concentration of 1.3 mg/mL. After allowing the plate to settle for 30 minutes at room temperature, radioactivity was quantitated on a microBeta counter (Model 1450, Wallec). The assay was also carried out without 5 mM potassium phosphate.

Gel Shift Assay

Twenty-four hours after planting 2×10$^6$ ras-transformed cells per treatment condition, the farnesylation inhibitor is added at varying concentrations. Following an 18-hour incubation period, cells are lysed in phosphate-buffered saline containing 1% Triton X-100, 0.5% sodium deoxycholate, and 0.1% SDS (sodium dodecyl sulfate), pH 7.4 in the presence of several protease inhibitors (PMSF (phenylmethylsulfonylfluoride), antipain, leupeptin, pepstatin A, and aprotinin all at 1 $\mu$g/mL). Ras protein is immunoprecipitated from the supernatants by the addition of 3 $\mu$g v-H-ras Ab-2 (Y13-259 antibody from Oncogene Science). After overnight immunoprecipitation, 30 $\mu$L of a 50% protein G-Sepharose slurry (Pharmacia) is added followed by 45-minute incubation. Pellets are resuspended in 2× tris-glycine loading buffer (Novex) containing 5% β-mercaptoethanol and then denatured by 5 minutes boiling prior to electrophoresis on 14% Tris-glycine SDS gels. Using Western transfer techniques, proteins are transferred to nitrocellulose membranes followed by blocking in blocking buffer. Upon overnight incubation with primary antibody (pan-ras Ab-2 from Oncogene Science), an antimouse HRP (horse radish peroxidase) conjugate secondary antibody (Amersham) is employed for detection of the ras protein. Blots are developed using ECL(enhanced chemiluminescence) techniques (Amersham).

Clonoaenic Assay (6 well lates)

Sometime previous to setting up an actual test:
1. Make up 1.5% Bacto Agar in Milli-Q water and autoclave.
2. Make up 500 mL 2× DMEM-HG without phenol red by combining the following:

1 bottle DMEM base powder (Sigma D-5030)
   4.5 g glucose
   3.7 g sodium bicarbonate
   0.11 g sodium pyruvate
   20 mL of 200 mM L-glutamine (Sigma G-7513)
   1 mL pen-strep (GibcoBRL No. 15140-023)
   Adjust pH to 7.1 with HCL; filter sterilize.

1. Set up makeshift water bath (beaker of water with thermometer, on hot plate) in the hood. Keep water temperature between 37° C. to 43° C.
2. Autoclave 1.5% Bacto Agar for approximately 2 minutes on high, or until completely melted. Then let it cool somewhat before using it. (You can keep it from resolidifying by setting the bottle on the hot plate.)

| 3. | Bottom Layer (0.6% agar) | Top Layer (0.3% agar) |
|---|---|---|
| | 20% calf serum | 20% calf serum |
| | 40% 2X DMEM | 50% 2X DMEM |
| | 40% Bacto Agar (1.5%) | 20% Bacto Agar (1.5%) |
| | | 10% sterile $H_2O \times \mu L$ |
| | | cell suspension (to = |
| | | 5000 cells/well) (H61 |
| | | cells: NIH transformed |
| | | 3T3 H-ras cells) |

Depending on the volume of each layer needed, use either 50 mL conical tubes or 200 mL turnip tubes which can be floated in the "water bath".

4. Add 1 mL of bottom layer agar/medium to each well: deliver 1 mL warm agar/medium to a well; then using the tip of the pipet, spread the agar/medium around to completely cover the bottom. Repeat with next well. Do Not add the last mL in the pipet to a well, it leads to bubbles.
5. Allow the plates to set at room temperature for about 5 minutes until the bottom layer solidifies.
6. Label sterile Falcon 2054 (12×75 mm) tubes and add appropriate volume of drug solutions into them.
7. Aliquot 4 AL of DMSO or drug solution per 1 mL of agar/medium to appropriate tubes; then add the agar/ medium/cells to each tube. Always add 1 mL more than will actually be needed. Mix up and down in the pipet (gently); then deliver 1 mL to the center of each well. The upper layer is less viscous, so it will generally spread out over the bottom layer unaided. If necessary, rotate the plane of the plate gently to spread the top layer evenly over the bottom layer.

8. Let plates set for 5 or 10 minutes at room temperature to solidify, then put into 5% $CO_2$, 37° C. incubator.
9. On Day 13, add 0.5 mL of INT (tetrazolium 1 mg/mL in Milli-Q $H_2O$, filter sterilized) and return plates to incubator.
10. Count colonies.

The data in the Table below shows farnesyl protein transferase inhibitory activity, and activity in the gel shift and clonogenic assays against ras protein of compounds of the present invention.

| Example No. | $IC_{50}$ ($\mu$M) Hepes | $IC_{50}$ ($\mu$M) 5 mM $K_3PO_4$-2 | Gel Shift ($\mu$M) MED* | Clonogenic Assay $IC_{50}$ ($\mu$M) |
|---|---|---|---|---|
| 1 | 7.7 | 0.26 | 1 | 2.7 (14.3) |
| 2 | 2.84 (2.1) | 0.024 (0.062) | 0.1 | 9.2 (4.33) |
| 3 | 3.1 (2.8) | 0.97 (0.61) | 0.25 | >1 |
| 4 | 5.8 (0.15) | 0.0076 (0.005) | 0.05 | >1 (0.31) |
| 5 | 1.73 (1.6) | 0.038 | 0.2 (0.05) | 0.71 (2.5) |
| 6 | 0.2 (0.5) | 0.0022 (0.017) | 0.2 | >1 |
| 7 | 9.8 | 0.36 | 0.1 | >1 |
| 8 | 7.8 | 0.30 | 0.2 | >1 |
| 9 | 4.5 | 0.36 | 0.2 | >1 |
| 10 | 0.58 | 0.018 | 0.01–0.05 | 0.71 |
| 11 | 2.5 | 0.082 | 0.2 | >1 |
| 12 | 1.1 | 0.062 | 0.2 | >1 |
| 13 | 1.4 | 0.022 | 0.2 | >1 |
| 14 | 1.6 | 0.066 | 0.05 | >1 |
| 15 | 0.12 | 0.007 | 0.01–0.05 | 0.19 |
| 16 | 0.29 | 0.007 | 0.01–0.05 | 0.40 |
| 17 | 2.8 | 0.086 | 0.2 | >1 |
| 18 | 2.8 | 0.061 | 0.2 | >1 |
| 19 | 1.26 | 0.015 | 0.05 | 0.66 |
| 20 | 1.5 | 0.017 | 0.05 | 0.46 |
| 21 | 0.16 | 0.008 | 0.05 | 0.30 |
| 22 | 1.2 | 0.016 | 0.2 | >1 |
| 23 | 1.6 | 0.022 | 0.2 | >1 |
| 24 | 0.20 | 0.014 | 0.2 | 0.82 |
| 25 | 0.93 | 0.032 | 0.2 | 0.89 |
| 26 | 0.15 | 0.009 | 0.2 | >1 |
| 27 | 0.12 | 0.014 | 0.2 | >1 |
| 28 | 2.6 | 0.043 | 0.2 | 0.6 |
| 29 | | | 0.1 | >1 |
| 30 | 0.78 | 0.016 | 0.1 | >1 |
| 31 | 0.52 | 0.014 | 0.1 | >1 |
| 32 | 0.32 | 0.007 | 0.05 | 0.36 |
| 33 | 0.50 | 0.009 | 0.05 | 0.36 |
| 34 | 0.097 | 0.002 | 0.05 | 0.14 |
| 35 | 2.1 | 0.009 | 0.2 | >1 |
| 36 | 0.45 | 0.007 | ≧0.05 | 0.32 |
| 37 | 0.92 | 0.026 | ≧0.2 | |
| 38 | 1.6 | 0.013 | 0.2 | 0.22 |
| 39 | 9.5 | 0.10 | >0.2 | >1 |
| 40 | 0.12 | 0.001 | 0.01 | 0.19 |
| 41 | 0.009 | 0.004 | 0.05 | 0.04 |
| 42 | 0.60 | 0.005 | 0.05 | 0.51 |
| 43 | 3.9 | 0.038 | 0.2 | >1 |
| 44 | 0.30 | 0.002 | 0.02 | 0.36 |
| 45 | 0.35 | 0.0024 | 0.05 | 0.14 |
| 46 | 1.98 | 0.034 | 1 | |
| 47 | 0.62 | 0.035 | 0.05 | 0.73 |
| 48 | 0.5 | 0.0029 | 0.05 | |
| 49 | 0.060 | 0.009 | 0.05 | 0.1 |
| 50 | 0.089 | 0.0010 | 0.05 | 0.27 |
| 51 | 0.88 | 0.004 | ≧0.05 | 0.25 |
| 52 | 0.48 | 0.004 | 0.05 | 0.52 |
| 53 | 10.6 | 0.12 | 0.2 | 12.4 |
| 54 | 0.20 | 0.0012 | 0.2 | |
| 55 | 0.86 | 0.014 | 0.05 | |
| 56 | 0.32 | 0.012 | 0.05 | |
| 57 | 0.38 | 0.0052 | | |
| 58 | 0.029 | 0.005 | 0.05 | |
| 59 | 0.52 | 0.004 | 0.05 | |
| 60 | 0.14 | 0.016 | 0.05 | |
| 61 | 0.66 | 0.018 | 0.01 | |
| 62 | 2.6 | 0.029 | | |

Numbers in parentheses indicate averages obtained by additional tests.
*MED is minimal effective dose to observe inhibition of ras farnesylation.

In Vivo Assay

The compound described in Example 15 was tested for its ability to inhibit the growth of H61 tumor cell xenografts in nude mice. H61 Cells are fibroblasts transformed to a malignant state by transfection with an activated mutant form of human h-ras. Ten to 30 mg fragments of H61 tumors were inoculated SC (subcutaneously) in the axial region into female nude mice with a trocar needle on day zero of the experiment. The mice were randomized to treatment groups and were then given SC injections of the compound described in Example 15 suspended in 10% cremofor/10% ethanol/80% water twice each day on Days 3–17 of the experiment. At Day 12 of the experiment, the median control tumor burden was 1958 mg as assessed by caliper measurements. The median tumor burden for animals treated with the compound described in Example 15 at 125 mg/kg/injection was 106 mg, indicating a 95% inhibition of tumor growth. The treatment regimen induced a tumor growth delay also consistent with significant inhibition of tumor growth at the 125 and 78 mg/kg/injection dose levels. These dose levels were well-tolerated with minimal or no host toxicity.

What is claimed is:
1. A compound having the Formula I

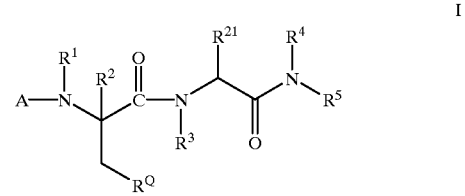

wherein $R^{21}$ is hydrogen or $C_1$–$C_6$ alkyl;

$R^Q$ is

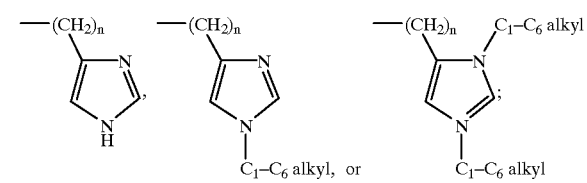

n is 0 or 1;

A is —COR$^a$, —CO$_2$R$^{a'}$, —CONHR$^{a'}$, —CSR$^a$,

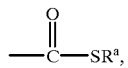

—C(S)OR$^{a'}$, —C(S)NHR$^{a'}$, —SO$_2$R$^a$, —CONR$^a$R$^{a''}$, or

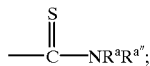

R$^a$, R$^{a'}$, and R$^{a''}$ are independently C$_1$–C$_6$ alkyl, —(CH$_2$)$_m$-cycloalkyl, —(CH$_2$)$_m$-aryl, or —(CH$_2$)$_m$-heteroaryl;

each m is independently 0 to 3;

R$^1$, R$^2$, and R$^4$ are independently hydrogen or C$_1$–C$_6$ alkyl;

R$^3$ is 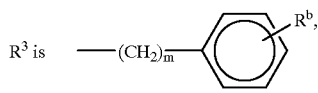

—(CH$_2$)$_m$-heteroaryl,

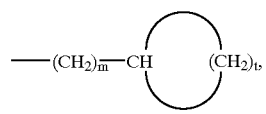

—(CH$_2$)$_m$-naphthyl, —(CH$_2$)$_m$-(heteroaryl substituted with R$^b$), or C$_1$–C$_6$ alkyl;

t is 2 to 6;

R$^b$ is —O-phenyl, —O-benzyl, halogen, C$_1$–C$_6$ alkyl, hydrogen, —OC$_1$–C$_6$ alkyl, —NH$_2$, —NHR$^a$, NR$^a$R$^{a'}$, —COC$_1$–C$_6$ alkyl, —C(O)—aryl, —OH, —CF$_3$, —NO$_2$, —COH, —COC$_1$–C$_6$ alkyl, —CN, —OPO$_3$H$_2$, —CH$_2$PO$_3$H$_2$, —COaryl, —N$_3$, —CF$_2$CF$_3$, —SO$_2$R$^a$, —SO$_2$NR$^a$R$^{a'}$, —CHO, —OCOCH$_3$, —O(CH$_2$)$_m$-heteroaryl, —CNR$^a$R$^{a'}$, —NH—CR$^a$, —SO$_2$R$^a$, —SO$_2$NR$^a$R$^{a'}$, —CHO, —OCOCH$_3$, —O(CH$_2$)$_m$-heteroaryl, —CNR$^a$R$^{a'}$, —NH—CR$^a$, —O—(CH$_2$)$_y$NR$^a$R$^{a'}$, —(CH$_2$)$_m$-aryl, —O—(CH$_2$)$_m$-aryl, —(CH$_2$)$_m$-heteroaryl, —O—(CH$_2$)$_m$-cycloalkyl, or —(CH$_2$)$_m$-cycloalkyl;

y is 2 or 3;

R$^5$ is

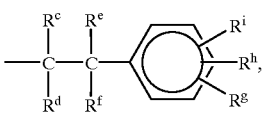
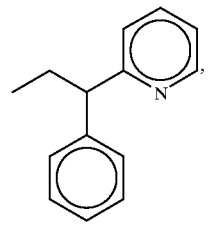
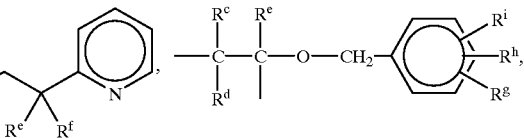
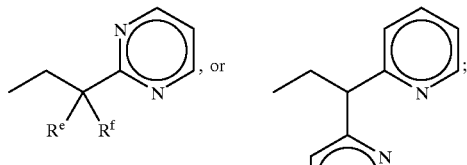

R$^i$, R$^g$, and R$^h$ are independently hydrogen, halogen, —OC$_1$–C$_6$ alkyl, C$_1$–C$_6$ alkyl, —CN, —OPO$_3$H$_2$, —CH$_2$PO$_3$H$_2$, —O-phenyl, —O-benzyl, —NH—C(O)—R$^a$, —NH$_2$, —NHR$^a$, —NR$^a$R$^{a'}$, —CC$_1$–C$_6$ alkyl, —C—aryl, —O—(CH$_2$)$_y$NR$^a$R$^{a'}$, —OH, —CF$_3$, —NO$_2$, —COH, —COC$_1$–C$_6$ alkyl, —CO aryl, —N$_3$, —CF$_2$CF$_3$, —SO$_2$R$^a$, —SO$_2$NR$^a$R$^{a'}$, —CHO, or —OCOCH$_3$; and R$^c$, R$^d$, R$^e$, and R$^f$ are independently C$_1$–C$_6$ alkyl, —(CH$_2$)$_m$-phenyl, hydrogen, —(CH$_2$)$_m$-OH, —(CH$_2$)$_m$-cycoalkcyl-(CH$_2$)$_m$NH$_2$, or —CN, provided that R$^g$, R$^h$ and R$^i$ are not all hydrogen when R$^{21}$, R$^4$ and R$^c$ to R$^f$ are all hydrogen, or the pharmaceutically acceptable salts, esters, amides, or prodrugs thereof.

2. A compound in accordance with claim 1 wherein

R$^1$ is hydrogen, R$^2$ is hydrogen, R$^4$ is hydrogen, R$^{21}$ is hydrogen or CH$_3$, and A is 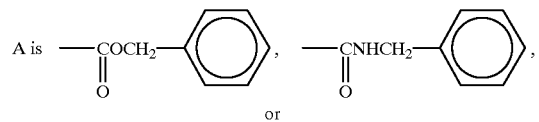

or

-continued

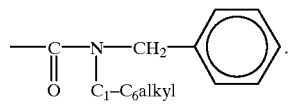

3. A compound in accordance with claim 1 wherein

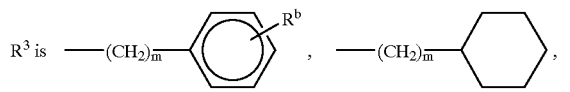

or —CH$_2$—CH(CH$_3$)$_2$.

R$^1$ is hydrogen, R$^2$ is hydrogen, R$^4$ is hydrogen, and R$^{21}$ is hydrogen or CH$_3$.

4. A compound according to claim 1 wherein R$^5$ is

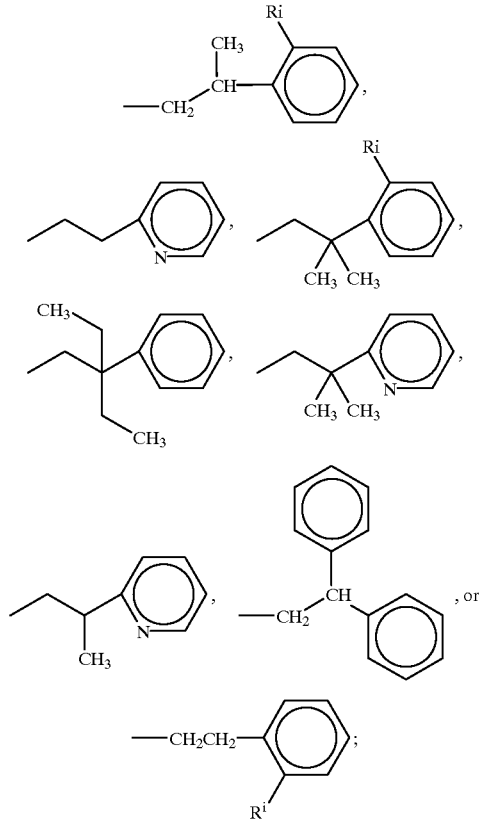

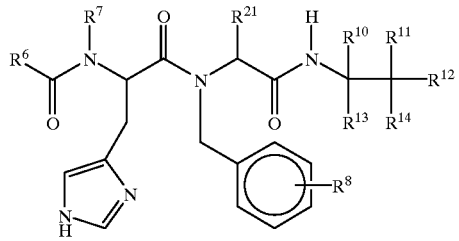

where R$^i$ is hydrogen, Cl, Br, F, or NH$_2$.

5. A compound having the Formula II

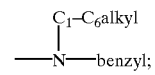

wherein

R$^6$ is —O-benzyl, —NH-benzyl, or

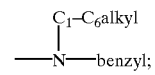

R$^{21}$ is hydrogen or methyl;

R$^7$ is hydrogen or methyl;

R$^8$ is hydrogen, halogen, C$_1$–C$_6$ alley, —O-benzyl, —OC$_1$–C$_6$ alkyl, —CF$_3$, —OH, or —O—(CH$_2$)$_m$-pyridyl, or phenyl;

R$^{10}$, R$^{11}$, R$^{13}$, and R$^{14}$ are independently hydrogen, C$_1$–C$_6$ alkyl, or —(CH$_2$)$_m$-phenyl;

each m is independently 0 to 3;

R$^{12}$ is

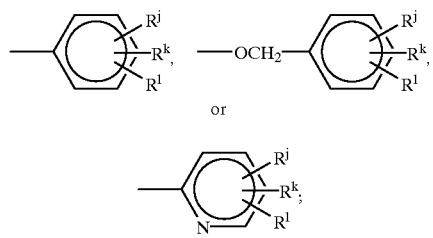

and

R$^j$, R$^k$, and R$^l$ are independently hydrogen, halogen, —OC$_1$–C$_6$ alkl or C$_1$–C$_6$ alkyl, —NHR$^a$, or NH$_2$, where R$^a$ is as defined in claim 1, provided that R$^j$ to R$^l$ are not all hydrogen when R$^{10}$, R$^{11}$, R$^{13}$ and R$^{14}$ are all hydrogen, or the pharmaceutically acceptable salts, esters, amides, or prodrugs thereof.

6. A compound in accordance with claim 5 wherein R$^{11}$ and R$^{14}$ are methyl.

7. A compound in accordance with claim 5 wherein R$^8$ is methyl or methoxy.

8. A compound having the Formula III

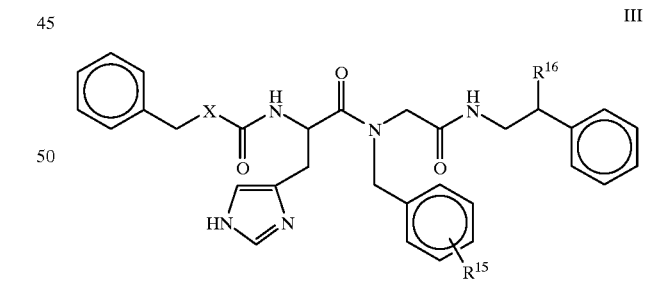

wherein

X is NH, O, or —N(CH$_3$);

R$^{15}$ is —O-benzyl, —CF$_3$, hydrogen, halogen, —OC$_1$–C$_6$ alkyl, phenyl, —O—CH$_2$-pyridyl, or C$_1$–C$_6$ alkyl;

m is 0 to 3; and

R$^{16}$ is a phenyl, hydrogen, or C$_1$–C$_6$ alkyl, cycloalkyl, or the pharmaceutically acceptable salts, esters, amides, or prodrugs thereof.

9. A compound having the Formula IV

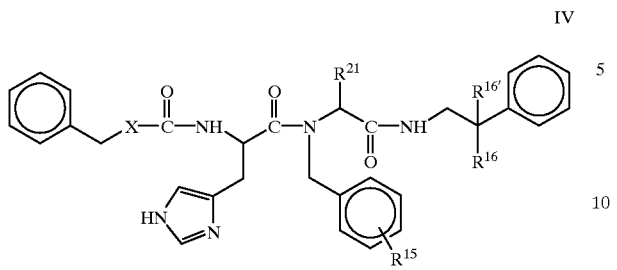

IV wherein
X is NH, O, or —N(CH$_3$);
R$^{15}$ is —O-benzyl, —CF$_3$, hydrogen, halogen, C$_1$–C$_6$ alkyl, —OC$_1$–C$_6$ alkyl, phenyl, or —O—(CH$_2$)$_m$-pyridyl;
R$^{16}$ and R$^{16'}$ are C$_1$–C$_6$ alkyl;
m is 0 to 3; and
R$^{21}$ is hydrogen or methyl, or the pharmaceutically acceptable salts, esters, amides, or prodrugs thereof.

10. A compound
(S)-[1-[(4-Benzyloxy-benzyl)-(phenethyl-carbamoyl-methyl)-carbamoyl]-2-(3H-imidazole-4-yl)-ethyl]-carbamic acid benzyl ester;
(S)-[1-[[2-Benzyloxy-ethylcarbamoyl]-methyl]-[4-chlorobenzyl]-carbamoyl]-2-(1H-imidazole-4-yl)-ethyl]-carbamic acid benzyl ester;
(S)-[1-[(4-Benzyloxy-benzyl)-[(2-phenyl-propyl-carbamoyl)-methyl]-carbamoyl]-2-(1H-imidazole-4-yl)-ethyl]carbamic acid benzyl ester;
(S)-[1-[(4-Benzyloxy-benzyl)-[(2,2-diphenyl-ethylcarbamoyl)-methyl]-carbamoyl]-2-(1H-imidazole-4-yl)-ethyl]-carbamic acid benzyl ester; or
(S)-N-(4-Benzyloxy-benzyl)-2-(3-benzyl-ureido)-3-(1H-imidazole-4-yl)-N-[(2-phenyl-propyl-carbamoyl)-methyl]-propionamide.

11. The compound
(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid benzyl ester.

12. A compound
(S)-[1-{Biphenyl-4-ylmethyl-[(2-methyl-2-phenyl-propylcarbamoyl)-methyl]-carbamoyl}-2-(1H-imidazole-4-yl)-ethyl]-carbamic acid benzyl ester;
(S)-[1-{Biphenyl-4-ylmethyl-[(2-phenyl-propylcarbamoyl)-methyl]-carbamoyl}-2-(1H-imidazole-4-yl)-ethyl]-carbamic acid benzyl ester;
(S)-[1-{(4-Benzyloxy-benzyl)-[(S)-(1-methyl-2-phenyl-ethylcarbamoyl)-methyl]-carbamoyl}-2-(1H-imidazole-4-yl)-ethyl]-carbamic acid benzyl ester;
(S)-[1-{(4-Benzyloxy-benzyl)-[(R)-(1-methyl-2-phenyl-ethylcarbamoyl)-methyl]-carbamoyl}-2-(1H-imidazole-4-yl)-ethyl]-carbamic acid benzyl ester;
(S)-[1-{(4-Benzyloxy-benzyl)-[(2-phenyl-butylcarbamoyl)-methyl]-carbamoyl}-2-(1H-imidazole-4-yl)-ethyl]-carbamic acid benzyl ester;
(S)-(2-(1H-Imidazole-4-yl)-1-{(4-methyl-benzyl)-[(2-phenyl-propylcarbamoyl)-methyl]-carbamoyl}-ethyl)-carbamic acid benzyl ester;
(S)-(2-(1H-Imidazole-4-yl)-1-{(4-methoxy-benzyl)-[(2-phenyl-propylcarbamoyl)-methyl]-carbamoyl}-ethyl)-carbamic acid benzyl ester;
(S)-[1-((4-Benzyloxy-benzyl)-{[2-(2-chloro-phenyl)-2-phenyl-ethylcarbamoyl]-methyl}-carbamoyl)-2-(1H-imidazole-4-yl)-ethyl]-carbamic acid benzyl ester;
(S)-[1-{(4-Benzyloxy-benzyl)-[(2-ethyl-2-phenyl-butylcarbamoyl)-methyl]-carbamoyl}-2-(3H-imidazole-4-yl)-ethyl]-carbamic acid benzyl ester;
(S)-[1-{(2-Chloro-benzyl)-[(2-phenyl-propylcarbamoyl)-methyl]-carbamoyl}-2-(1H-imidazole-4-yl)-ethyl]-carbamic acid benzyl ester;
(S)-[1-((4-Benzyloxy-benzyl)-{[2-(2-chloro-phenyl)-propylcarbamoyl]-methyl}-carbamoyl)-2-(1H-imidazole-4-yl)-ethyl]-carbamic acid benzyl ester;
(S)-(2-(1H-Imidazole-4-yl)-1-{(2-methoxy-benzyl)-[(2-phenyl-propylcarbamoyl)-methyl]-carbamoyl}-ethyl)-carbamic acid benzyl ester;
(S)-(2-(1H-Imidazole-4-yl)-1-{[(2-phenyl-propylcarbamoyl)-methyl]-[4-(pyridin-4-ylmethoxy)-benzyl]-carbamoyl}-ethyl)-carbamic acid benzyl ester;
(S)-(2-(1H-Imidazole-4-yl)-1-{[(2-phenyl-propylcarbamoyl)-methyl]-[4-(pyridin-3-ylmethoxy)-benzyl]-carbamoyl}-ethyl)-carbamic acid benzyl ester;
(S)-[2-(1H-Imidazole-4-yl)-1-[[(2-phenyl-propylcarbamoyl)-methyl]-(4-trifluoromethyl-benzyl)-carbamoyl]-ethyl}-carbamic acid benzyl ester;
(S)-(2-(1H-Imidazole-4-yl)-1-{[(2-methyl-2-phenyl-propylcarbamoyl)-methyl]-[4-(pyridin-2-ylmethoxy)-benzyl]-carbamoyl}-ethyl)-carbamic acid benzyl ester;
(S)-[1-{Benzyl-[(2-methyl-2-phenyl-propyl-carbamoyl)-methyl]-carbamoyl}-2-(1H-imidazole-4-yl)-ethyl]-carbamic acid benzyl ester;
(S) (2-(1H-Imidazole-4-yl)-1-{(4-methoxy-benzyl)-[(2-methyl-2-phenyl-propylcarbamoyl)-methyl]-carbamoyl}-ethyl]-carbamic acid benzyl ester;
(S)-[1-{(4-Benzyloxy-benzyl)-[(2-cyano-2-phenyl-ethylcarbamoyl)-methyl]-carbamoyl}-2-(1H-imidazole-4-yl)-ethyl]-carbamic acid benzyl ester;
(S)-2-(3-Benzyl-3-methyl-ureido)-N-(4-benzyloxy-benzyl)-3-(1H-imidazole-4-yl)-N-[(2-methyl-2-phenyl-propylcarbamoyl)-methyl]-propionamide;
(S)-[1-[{[2-(2-Amino-phenyl)-propylcarbamoyl]-methyl}-(4-benzyloxy-benzyl)-carbamoyl]-2-(3H-imidazole-4-yl)-ethyl]-carbamic acid benzyl ester;
(S)-(2-(1H-Imidazole-4-yl)-1-{[(2-methyl-2-phenyl-propylcarbamoyl)-methyl]-[4-(pyridin-4-ylmethoxy)-benzyl]-carbamoyl}-ethyl)-carbamic acid benzyl ester;
(S)-(2-(1H-Imidazole-4-yl)-1-{[(2-methyl-2-phenyl-propylcarbamoyl)-methyl]-[4-(pyridin-3-ylmethoxy)-benzyl]-carbamoyl}-ethyl)-carbamic acid benzyl ester; or
(S)-[1-{Cyclohexylmethyl-[(2-phenyl-propylcarbamoyl)-methyl]-carbamoyl}-2-(3H-imidazole-4-yl)-ethyl]-carbamic acid benzyl ester.

13. A compound
(S)-[1-((4-Benzyloxy-benzyl)-{[2-(2-fluoro-phenyl)-ethylcarbamoyl]-methyl}-carbamoyl)-2-(1H-imidazole-4-yl)-ethyl]-carbamic acid benzyl ester;
(S)-[1-{(4-Benzyloxy-benzyl)-[(2-pyridin-2-yl-ethylcarbamoyl)-methyl]-carbamoyl}-2-(1H-imidazole-4-yl)-ethyl]-carbamic acid benzyl ester;
(S)-[1-((4-Benzyloxy-benzyl)-{[2-(2-bromo-phenyl)-ethylcarbamoyl]-methyl}-carbamoyl)-2-(1H-imidazole-4-yl)-ethyl]-carbamic acid benzyl ester;
(S)-[1-{(4-Benzyloxy-benzyl)-[(2-phenyl-2-pyridin-2-yl-ethylcarbamoyl)-methyl]-carbamoyl}-2-(1H-imidazole-4-yl)-ethyl]-carbamic acid benzyl ester;

(S)-[1-{(4-Chloro-benzyl)-[(2-phenyl-propylcarbamoyl)-methyl]-carbamoyl}-2-(1H-imidazole-4-yl)-ethyl]-carbamic acid benzyl ester;

(S)-N-(4-Benzyloxy-benzyl)-3-(1H-imidazole-4-yl)-2-(3-phenyl-propionylamino)-N-[(2-phenyl-propylcarbamoyl)-methyl]-propionamide;

(S)-[1-{(4-Fluoro-benzyl)-[(2-phenyl-propyl-carbamoyl)-methyl]-carbamoyl}-2-(1H-imidazole-4-yl)-ethyl]-carbamic acid benzyl ester;

(S)-[1-{(4-Fluoro-benzyl)-[(2-methyl-2-phenyl-propylcarbamoyl)-methyl]-carbamoyl}-2-(1H-imidazole-4-yl)-ethyl]-carbamic acid benzyl ester;

(S)-[1-{Benzyl-[(2-phenyl-propylcarbamoyl)-methyl]-carbamoyl}-2-(1H-imidazole-4-yl)-ethyl]-carbamic acid benzyl ester;

(S)-N-(4-Benzyloxy-benzyl)-2-(3-benzyl-ureido)-3-(1H-imidazole-4-yl)-N-[(2-phenyl-propylcarbamoyl)-methyl]-propionamide;

(S)-N-(4-Benzyloxy-benzyl)-2-(3-benzyl-ureido)-3-(1H-imidazole-4-yl)-N-[(2-phenyl-butylcarbamoyl)-methyl]-propionamide;

(S)-[1-{(4-Bromo-benzyl)-[(2-phenyl-propylcarbamoyl)-methyl]-carbamoyl}-2-(1H-imidazole-4-yl)-ethyl]-carbamic acid benzyl ester;

(S)-[1-{(3-Chloro-benzyl)-[(2-phenyl-propylcarbamoyl)-methyl]-carbamoyl}-2-(1H-imidazole-4-yl)-ethyl]-carbamic acid benzyl ester;

(S)-[1-{(4-Chloro-benzyl)-[(2-methyl-2-phenyl-propylcarbamoyl)-methyl]-carbamoyl}-2-(1H-imidazole-4-yl)-ethyl]-carbamic acid benzyl ester;

(S)-(2-(1H-Imidazole-4-yl)-1-{(3-methoxy-benzyl)-[(2-phenyl-propylcarbamoyl)-methyl]-carbamoyl}-ethyl)-carbamic acid benzyl ester;

(S)-(2-(1H-Imidazole-4-yl)-1-{naphthalen-1-ylmethyl-[(2-phenyl-propylcarbamoyl)-methyl]-carbamoyl}-ethyl)-carbamic acid benzyl ester;

(S)-(2-(1H-Imidazole-4-yl)-1-{[(2-methyl-2-phenyl-propylcarbamoyl)-methyl]-pyridin-3-ylmethyl-carbamoyl}-ethyl)-carbamic acid benzyl ester;

(S)-(2-(1H-Imidazole-4-yl)-1-{(2-methyl-benzyl)-[(2-phenyl-propylcarbamoyl)-methyl]-carbamoyl}-ethyl)-carbamic acid benzyl ester;

(S)-(2-(1H-Imidazole-4-yl)-1-{[(2-methyl-2-phenyl-propylcarbamoyl)-methyl]-pyridin-2-ylmethyl-carbamoyl}-ethyl)-carbamic acid benzyl ester;

(S)-(2-(1H-Imidazole-4-yl)-1-{(3-methyl-benzyl)-[(2-phenyl-propylcarbamoyl)-methyl]-carbamoyl}-ethyl)-carbamic acid benzyl ester;

(S)-[1-{(4-Dimethylamino-benzyl)-[(2-phenyl-propylcarbamoyl)-methyl]-carbamoyl}-2-(1H-imidazole-4-yl)-ethyl]-carbamic acid benzyl ester;

(S)-[1-{(4-Benzyloxy-benzyl)-[(2-hydroxy-2-phenyl-ethyl-carbamoyl)-methyl]-carbamoyl}-2-(3H-imidazo-4-yl)-ethyl]-carbamic acid benzyl ester;

(S)-[1-((4-Benzyloxy-benzyl)-{[2-(2-chloro-phenyl)-ethylcarbamoyl]methyl}-carbamoyl)-2-(1H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(1H-imidazole-4-yl)-ethyl]-carbamic acid thiophen-3-ylmethyl ester;

(S)-[1-{(4-Chloro-benzyl)-[1-(2-methyl-2-phenyl-propylcarbamoyl)-ethyl]-carbamoyl}-2-(3H-imidazole-4-yl)-ethyl]-carbamic acid benzyl ester;

(S)-(2-(1H-Imidazole-4-yl)-1-{(4-methyl-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{(2-methoxy-benzyl)-[(2-methyl-2-phenyl-propylcarbamoyl)-methyl]-carbamoyl}-ethyl)-carbamic acid benzyl ester;

(S)-2-(3-Benzyl-3-methyl-ureido)-N-(4-chloro-benzyl)-3-(1H-imidazole-4-yl)-N-[(2-methyl-2-phenyl-propylcarbamoyl)-methyl]-propionamide;

(S)-(2-(1H-Imidazole-4-yl)-1-{(3-methoxy-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{[(2-methyl-2-phenyl-propylcarbamoyl)-methyl]-[2-(pyridin-4-ylmethoxy)-benzyl]-carbamoyl}-ethyl)-carbamic acid benzyl ester; or (2-(1H-Imidazol-4-yl)-1-{isobutyl-[(2-phenyl-propylcarbamoyl)-methyl]-carbamoyl}-ethyl)-carbamic acid benzyl ester.

14. A compound (S)-[1-{(4-Benzyloxy-benzyl)-[(2-phenyl-pentyl-carbamoyl)-methyl]-carbamoyl}-2-(3H-imidazole-4-yl)-ethyl]-carbamic acid benzyl ester;

(S)-[1-{[2-(4-Benzyloxy-phenyl)-ethyl]-[(2-methyl-2-phenyl-propylcarbamoyl)-methyl]-carbamoyl}-2-(3H-imidazole-4-yl)-ethyl]-carbamic acid benzyl ester;

(S)-(2-(3H-Imidazole-4-yl)-1-{[2-(4-methoxy-phenyl)-ethyl]-[(2-methyl-2-phenyl-propyl-carbamoyl)-methyl]-carbamoyl}-ethyl)-carbamic acid benzyl ester;

(S)-[1-[{[2-(2-Amino-phenyl)-ethylcarbamoyl]-methyl}-(4-benzyloxy-benzyl)-carbamoyl]-2-(3H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-methyl-carbamic acid benzyl ester;

(S)-[1-{(4-Benzyloxy-benzyl)-[(2-methyl-2-phenyl-propylcarbamoyl)-methyl]-carbamoyl}-2-(3-methyl-3H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(1-methyl-1H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid furan-2-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid thiophen-2-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid pyridin-3-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid 1H-imidazole-4-ylmethyl ester;

(S)-2-(3-Benzyl-ureido)-N-(4-chloro-benzyl)-3-(3H-imidazole-4-yl)-N-[(2-methyl-2-phenyl-propyl-carbamoyl)-methyl]-propionamide;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid 4-methoxy-benzyl ester;

(S)-2-(3-Benzyl-thioureido)-3-(3H-imidazole-4-yl)-N-(4-methyl-benzyl)-N-[(2-methyl-2-phenyl-propylcarbamoyl)-methyl]-propionamide;

(S)-2-Acetylamino-N-(4-benzyloxy-benzyl)-3-(3H-imidazole-4-yl)-N-[(2-methyl-2-phenyl-propylcarbamoyl)-methyl]-propionamide;

(S)-(2-(3H-Imidazole-4-yl)-1-{[(2-methyl-2-phenyl-propylcarbamoyl)-methyl]-pyridin-4-ylmethyl-carbamoyl}-ethyl)-carbamic acid benzyl ester;

(S)-{2-(3H-Imidazole-4-yl)-1-[(4-iodo-benzyl)-(phenethylcarbamoyl-methyl)-carbamoyl]-ethyl}-carbamic acid benzyl ester;

(S)-[1-{(4-Amino-benzyl)-[(2-methyl-2-phenyl-propylcarbamoyl)-methyl]-carbamoyl}-2-(3H-imidazole-4-yl)-ethyl]-carbamic acid benzyl ester;

(S)-[1-{(4-Ethoxy-benzyl)-[(2-methyl-2-phenyl-propylcarbamoyl)-methyl]-carbamoyl}-2-(3H-imidazole-4-yl)-ethyl]-carbamic acid benzyl ester;

(S)-[1-{[4-(2-Dimethylamino-ethoxy)-benzyl]-[(2-methyl-2-phenyl-propylcarbamoyl)-methyl]-carbamoyl}-2-(3H-imidazole-4-yl)-ethyl]-carbamic acid benzyl ester; and (2-(1H-imidazole-4-yl)-1-{isobutyl-[(2-methyl-2-phenyl-propyl carbamoyl)-methyl]-carbamoyl}-ethyl)-carbamic acid benzyl ester.

15. A pharmaceutically acceptable composition that comprises a compound of claim 1.

16. A pharmaceutically acceptable composition that comprises a compound of claim 5.

17. A pharmaceutically acceptable composition that comprises a compound of claim 6.

18. A method of inhibiting protein farnesyl transferase in a patient, the method comprising administering to a patient an effective amount of a compound of claim 1.

19. A method of inhibiting protein farnesyl transferase in a patient, the method comprising administering to a patient an effective amount of a compound of claim 5.

20. A method of inhibiting protein farnesyl transferase in a patient, the method comprising administering to a patient an effective amount of a compound of claim 6.

21. A method of treating or preventing restenosis, the method comprising administering to a patient having restenosis or at risk of having restenosis a therapeutically effective amount of a compound of claim 1.

22. A method of treating or preventing restenosis, the method comprising administering to a patient having restenosis or at risk of having restenosis a therapeutically effective amount of a compound of claim 5.

23. A method of treating or preventing restenosis, the method comprising administering to a patient having restenosis or at risk of having restenosis a therapeutically effective amount of a compound of claim 6.

24. A method of treating a viral infection, the method comprising administering to a patient having a viral infection a therapeutically effective amount of a compound of claim 1.

25. A method of treating a viral infection, the method comprising administering to a patient having a viral infection a therapeutically effective amount of a compound of claim 5.

26. A method of treating a viral infection, the method comprising administering to a patient having a viral infection a therapeutically effective amount of a compound of claim 6.

27. A method of treating psoriasis, the method comprising administering to a patient having psoriasis a therapeutically effective amount of a compound of claim 1.

28. A method of treating psoriasis, the method comprising administering to a patient having psoriasis a therapeutically effective amount of a compound of claim 5.

29. A method of treating psoriasis, the method comprising administering to a patient having psoriasis a therapeutically effective amount of a compound of claim 6.

* * * * *

UNITED STATES PATENT AND TRADEMARK OFFICE
CERTIFICATE OF CORRECTION

PATENT NO. : 6,300,501 B1
DATED : October 9, 2001
INVENTOR(S) : Ellen M. Dobrusin et al.

It is certified that error appears in the above-identified patent and that said Letters Patent is hereby corrected as shown below:

Column 48,
Line 64,

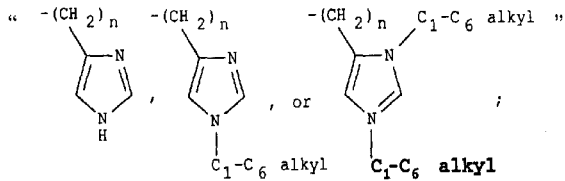

should read

-- 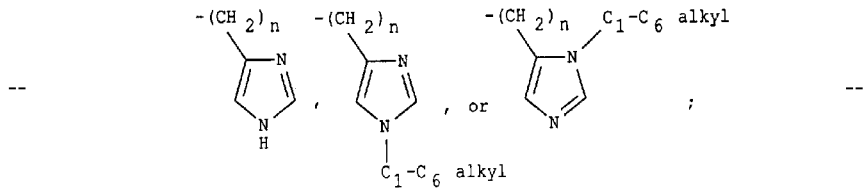 --

Column 49,
Line 57, delete "—$SO_2R^a$,—$SO_2NR^aR^a$,—CHO, —$OCOCH_3$, —$O(CH_2)_m$-heteroaryl, 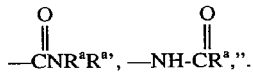".

UNITED STATES PATENT AND TRADEMARK OFFICE
CERTIFICATE OF CORRECTION

PATENT NO. : 6,300,501 B1
DATED : October 9, 2001
INVENTOR(S) : Ellen M. Dobrusin et al.

It is certified that error appears in the above-identified patent and that said Letters Patent is hereby corrected as shown below:

<u>Column 52,</u>
Line 10, "$R^8$ is hydrogen, halogen, $C_1$-$C_6$ alley, -O-benzyl," should read -- $R^8$ is hydrogen, halogen, $C_1$-$C_6$ alkyl, -O-benzyl, --.
Line 33, "halogen, -O$C_1$-$C_6$ alkl or $C_1$-$C_6$ alkyl, -NHR$^a$, or NH$_2$," should read -- halogen, -O$C_1$-$C_6$ alkyl or $C_1$-$C_6$ alkyl, -NHR$^a$, or NH$_2$, --.

Signed and Sealed this

Twenty-fifth Day of March, 2003

JAMES E. ROGAN
*Director of the United States Patent and Trademark Office*